United States Patent
Budijono et al.

(10) Patent No.: US 9,487,733 B2
(45) Date of Patent: Nov. 8, 2016

(54) METHOD TO IMPROVE THE PERFORMANCE OF ENCAPSULATED FRAGRANCES

(71) Applicant: FIRMENICH SA, Geneva (CH)

(72) Inventors: Stéphanie Budijono, New York, NY (US); Lahoussine Ouali, Geneva (CH); Valery Normand, Plainsboro, NJ (US); Jean-Yves Billard De Saint Laumer, Geneva (CH); Suying Zhang, Plainsboro, NJ (US)

(73) Assignee: Firmenich SA, Geneva (CH)

( * ) Notice: Subject to any disclaimer, the term of this patent is extended or adjusted under 35 U.S.C. 154(b) by 75 days.

(21) Appl. No.: 14/423,064

(22) PCT Filed: Aug. 16, 2013

(86) PCT No.: PCT/EP2013/067121
§ 371 (c)(1),
(2) Date: Jun. 15, 2015

(87) PCT Pub. No.: WO2014/029695
PCT Pub. Date: Feb. 27, 2014

(65) Prior Publication Data
US 2015/0284660 A1    Oct. 8, 2015

(30) Foreign Application Priority Data

Aug. 21, 2012  (WO) ............... PCT/US2012/051725

(51) Int. Cl.
*C11B 9/00* (2006.01)
*A61Q 13/00* (2006.01)
(Continued)

(52) U.S. Cl.
CPC ............ *C11B 9/0019* (2013.01); *A61K 8/11* (2013.01); *A61K 8/33* (2013.01); *A61K 8/342* (2013.01);
(Continued)

(58) Field of Classification Search
CPC .................................................. C11B 9/0019

USPC ............................................................. 512/4
See application file for complete search history.

(56) References Cited

U.S. PATENT DOCUMENTS 4,081,384 A    3/1978  Pracht
4,137,180 A    1/1979  Naik et al.
(Continued)

FOREIGN PATENT DOCUMENTS

DE    102008059448 A1    6/2010
EP         799885 A1    10/1997
(Continued)

OTHER PUBLICATIONS

International Search Report and Written Opinion, application PCT/EP2013/067121 mailed Nov. 25, 2013.
(Continued)

*Primary Examiner* — Ling Choi
*Assistant Examiner* — Lanee Reuther
(74) *Attorney, Agent, or Firm* — Winston & Strawn LLP

(57) ABSTRACT

The invention relates to a perfume composition that includes a first perfume microcapsule encapsulating a first perfume oil that has a LogT greater than −2.5 and a cLogP greater than 2.5 and/or a volatility value of at least 30 μg/l air; and a second perfume microcapsule encapsulating a second perfume oil ingredient that has a LogT less than −2.5 and a cLogP greater than 2.5 and/or a volatility value of at least 30 μg/l air. The invention also relates to the use of such mixtures of microcapsules as a perfuming ingredient or perfuming composition for home or personal care products, as well as to the resulting home and body care compositions. Also, a method for increasing shelf life of a home- or personal-care product that contains a perfuming composition which comprises providing the perfume composition as one of the mixtures of microcapsules disclosed herein.

14 Claims, 6 Drawing Sheets

(51) Int. Cl.

| | | |
|---|---|---|
| A61K 8/11 | (2006.01) | |
| C11D 3/50 | (2006.01) | |
| A61Q 5/02 | (2006.01) | |
| A61Q 5/12 | (2006.01) | |
| A61Q 15/00 | (2006.01) | |
| A61K 8/92 | (2006.01) | |
| A61K 8/33 | (2006.01) | |
| A61K 8/34 | (2006.01) | |
| A61K 8/35 | (2006.01) | |
| A61K 8/37 | (2006.01) | |
| A61K 8/49 | (2006.01) | |
| A61Q 19/10 | (2006.01) | |
| C11D 3/20 | (2006.01) | |
| C11D 3/34 | (2006.01) | |

(52) U.S. Cl.
CPC . *A61K 8/35* (2013.01); *A61K 8/37* (2013.01); *A61K 8/49* (2013.01); *A61K 8/922* (2013.01); *A61Q 5/02* (2013.01); *A61Q 5/12* (2013.01); *A61Q 13/00* (2013.01); *A61Q 15/00* (2013.01); *A61Q 19/10* (2013.01); *C11B 9/008* (2013.01); *C11B 9/0015* (2013.01); *C11B 9/0034* (2013.01); *C11B 9/0046* (2013.01); *C11D 3/2072* (2013.01); *C11D 3/2093* (2013.01); *C11D 3/3481* (2013.01); *C11D 3/505* (2013.01); *A61K 2800/412* (2013.01); *A61K 2800/591* (2013.01)

(56) References Cited

U.S. PATENT DOCUMENTS

| | | | |
|---|---|---|---|
| 4,234,627 | A | 11/1980 | Schilling |
| 4,514,461 | A | 4/1985 | Woo |
| 4,882,220 | A | 11/1989 | Ono et al. |
| 4,917,920 | A | 4/1990 | Ono et al. |
| 5,145,842 | A | 9/1992 | Driedger et al. |
| 5,236,615 | A | 8/1993 | Trinh et al. |
| 6,200,949 | B1 | 3/2001 | Reijmer et al. |
| 6,458,754 | B1 | 10/2002 | Velazquez et al. |
| 6,544,926 | B1 | 4/2003 | Bodmer et al. |
| 6,592,990 | B2 | 7/2003 | Schwantes |
| 6,645,479 | B1 | 11/2003 | Shefer et al. |
| 7,119,057 | B2 | 10/2006 | Popplewell et al. |
| 8,426,353 | B2 | 4/2013 | Ouali et al. |
| 2003/0158344 | A1 | 8/2003 | Rodriques et al. |
| 2003/0165692 | A1 | 9/2003 | Koch et al. |
| 2003/0195133 | A1 | 10/2003 | Shefer et al. |
| 2003/0203829 | A1 | 10/2003 | Shefer et al. |
| 2003/0215417 | A1 | 11/2003 | Uchiyama et al. |
| 2003/0216488 | A1 | 11/2003 | Uchiyama et al. |
| 2004/0071742 | A1 | 4/2004 | Popplewell et al. |
| 2004/0071746 | A1 | 4/2004 | Popplewell et al. |
| 2004/0072719 | A1 | 4/2004 | Bennett et al. |
| 2004/0072720 | A1 | 4/2004 | Brain et al. |
| 2004/0087477 | A1 | 5/2004 | Ness |
| 2004/0106536 | A1 | 6/2004 | Mane et al. |
| 2007/0179082 | A1* | 8/2007 | Morgan, III ............ C11D 3/50 510/515 |
| 2008/0305982 | A1 | 12/2008 | Smets et al. |
| 2009/0186096 | A1 | 7/2009 | Kritzman et al. |
| 2009/0247449 | A1 | 10/2009 | Burdis et al. |
| 2011/0245141 | A1 | 10/2011 | Gizaw et al. |

FOREIGN PATENT DOCUMENTS

| | | |
|---|---|---|
| WO | WO9734986 A1 | 9/1997 |
| WO | WO 2007135636 A1 | 11/2007 |
| WO | WO2011075353 A1 | 6/2011 |
| WO | WO2011094681 A1 | 8/2011 |

OTHER PUBLICATIONS

C. Vuilleumier et al., Perfumer & Flavorist, Sep. 2008, vol. 33, p. 54-61.
A. Leo, Comprehensive Medicinal Chemistry, Pergamon Press 1990, vol. 4, p. 295.
Ullman's Encyclopedia of Industrial Chemistry, vol. A8, 1987, p. 315-448.
Ullman's Encyclopedia of Industrial Chemistry, vol. A25, 1994, p. 747-817.

* cited by examiner

METHOD TO IMPROVE THE PERFORMANCE OF ENCAPSULATED FRAGRANCES

TECHNICAL FIELD

The invention relates to perfume compositions comprising hybrid fragrance microcapsules and home and personal care product compositions containing such microcapsules along with surfactants and other conventional ingredients.

BACKGROUND OF THE INVENTION

Perfume additives make laundry compositions more aesthetically pleasing to the consumer, and in some cases the perfume imparts a pleasant fragrance to fabrics treated therewith. The amount of perfume carryover from an aqueous laundry bath onto fabrics, however, is often marginal. By encapsulating perfume additives in microcapsules, the delivery efficiency and active lifetime of the perfume additives can be improved. Microcapsules provide several advantages, such as protecting the perfumes from physical or chemical reactions with incompatible ingredients in the laundry composition, and from volatilization or evaporation. Microcapsules can be particularly effective in the delivery and preservation of perfumes in that perfumes can be delivered to and retained within the fabric by a microcapsule that only ruptures, and therefore releases the perfume, when the fabric is dry. The rupture of microcapsules can be induced by various factors such as temperature so that the contents are delivered when the capsule degrades. Alternatively the microcapsules can be compromised by physical forces, such as crushing, or other methods that compromise the integrity of the microcapsules. Additionally, the microcapsule contents may be delivered via diffusion through the capsule wall during a desired time interval.

Scent associated with laundered laundry is important to many consumers. There are many so called "touch points" that consumers associate with during the laundry experience. Non-limiting examples of these touch points include the freshness experience associated with opening a fabric care container, opening a washing machine after washing laundry, opening a laundry dryer after drying laundry, and freshness associated with wearing laundered clothes. It has been reported that there is a significant portion of consumers that will fold and put away their laundry about one day after having laundered laundry. Freshness while folding laundry about one day after having laundered laundry also signals to the consumer that the laundry is clean.

Several compositions have been proposed to provide fragrances at various "touch points" of the laundering process. For example, WO 2011/094681 discloses fabric softening compositions comprising two different encapsulated perfume compositions to provide an improved laundry experience to consumers. These two different encapsulated perfume compositions each contains a specific mix of perfume ingredients having a boiling point (at standard pressure) greater than 250° C. and perfume ingredients having a boiling point lower than 250° C.

Instead of using two different encapsulated perfume compositions, WO 2011/075353 discloses a liquid detergent composition comprising a single type of perfume microcapsules which contains two different perfume raw materials, with one having a boiling point less than 250° C. and the other having a boiling point greater than 250° C.

It has been shown that the boiling point of a perfume ingredient, which is frequently used as an indication for its volatilization rate, does not correlate with its odor threshold concentration, i.e., the lowest concentration of the perfume ingredient that is perceivable by the human sense of smell. Therefore, selection of perfume ingredients based only on physical properties such as boiling points does not always provide the desired effect.

Thus, there is a need in the industry for compositions comprising perfume ingredients having different biological properties such as odor threshold concentrations, which release perfumes at the right level for the desired duration and time points during the laundering process to provide consumers with a delightful experience. There is also a need to improve the perfume release or diffusion in personal care applications. The present invention satisfies this and other needs of the industry.

SUMMARY OF THE INVENTION

One embodiment of the present invention relates to a perfume composition comprising a mixture of microcapsules including (a) a first perfume microcapsule encapsulating a first perfume oil that has a LogT greater than −2.5 and a cLogP greater than 2.5 and/or a volatility value of at least 30 µg/l air; and (b) a second perfume microcapsule encapsulating a second perfume oil that has a LogT less than −2.5 and a cLogP greater than 2.5 and/or a volatility value of at least 30 µg/l air. Advantageously, either of the first or the second perfume oil, or both, comprises a single perfuming compound or a mixture of perfuming compounds wherein preferably at least 80%, more preferably 100% of the perfuming compounds has individually the recited LogT, cLogP and/or volatility values. Also, the compound or compounds in the first or the second perfume oil, or both, each may have a boiling point of either 250° C. to 450° C. or of 100° C. to 250° C., as desired depending upon the application. Alternatively, the compound or compounds in the first or the second perfume oil ingredients, or both, each separately have a volatility value of 30 to $5 \times 10^5$ µg/l air.

Preferably, the first or second or both perfume microcapsule(s) have a core/shell structure wherein the encapsulating material forms the shell while the perfume oil form the core, wherein one of the first or second microcapsules (a) has a wall made of a different resin than the other; (b) has a wall that includes a different amount of resin or monomer than the other; or (c) contains a different amount perfume oil ingredient than the other. Alternatively, one microcapsule can have a core/shell structure while the other has a matrix structure to provide different rates of releases of the perfume oil.

In a more preferred embodiment, the first microcapsule contains 50% by weight or less of the first perfume oil with each compound of the first perfume oil separately having a boiling point of 250° C. to 450° C., while the second microcapsule contains 50% by weight or more of the second perfume oil with each compound of the second perfume oil separately having a boiling point of 100° C. to 250° C.

The invention also relates to the use of one of the mixtures of microcapsules disclosed herein as a perfuming ingredient or composition, for home- or personal-care products.

Another embodiment of the invention is a consumer product in the form of a home- or personal-care product that includes a perfume composition as described herein. This product can be in the form of a detergent composition, a fabric softener, a hard surface or all purpose cleaning composition. It also could be in the form of a shampoo, a hair conditioner, a shower or bath mousse, oil or gel, a deodorant, or an antiperspirant.

Yet another embodiment of the invention is a method for increasing shelf life of a home- or personal-care product that contains a perfuming composition which comprises providing the perfume composition as one of the mixtures of microcapsules disclosed herein.

DETAILED DESCRIPTION OF THE INVENTION

Figure 1A:
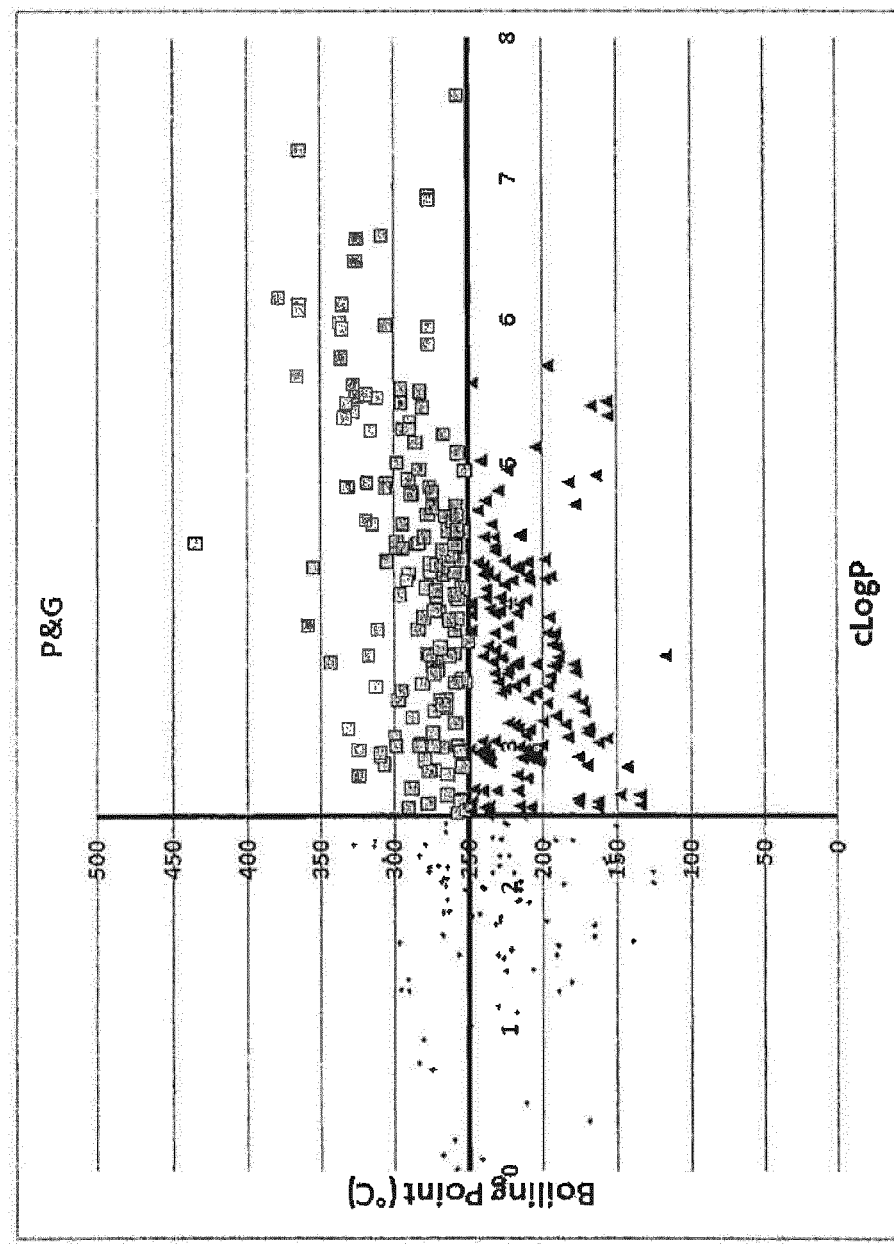
FIGS. 1A and B are graphs showing the boiling points (A) and the odor threshold concentrations (B) of the prior art perfume ingredients.
Figure 1B:
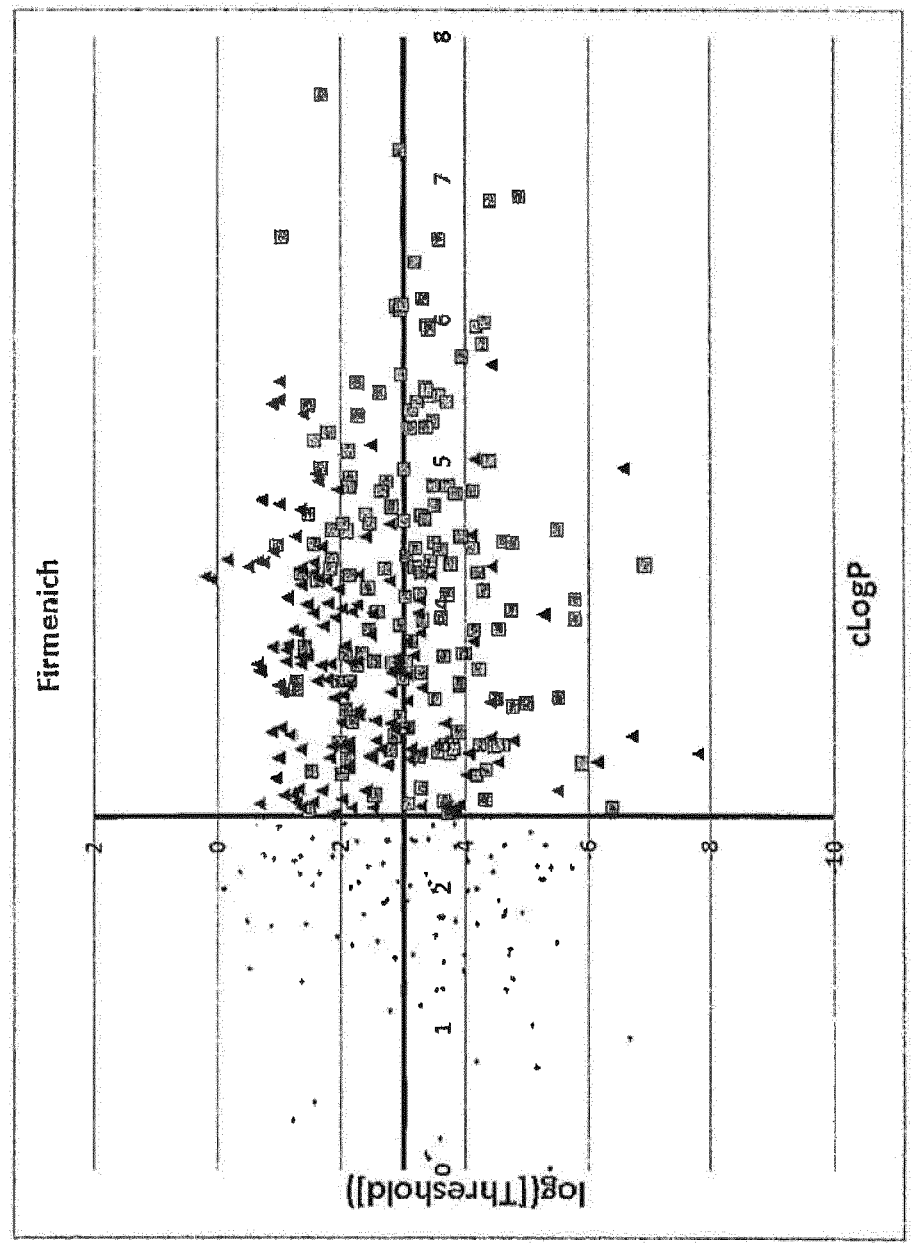

The present invention now has determined an improved way to provide different release times and scents of fragrance materials in various products. If all perfume raw materials are encapsulated in the same microcapsules, some materials are released at too high of a dosage and this causes the product to smell too functional and more like a raw material. Also, splitting the perfuming compounds of an oil into different capsules according to their boiling point has been found to not be optimal to provide the best delivery and hedonic effect one may expect from the perfuming oil. It has now been discovered that it is not sufficient to simply mix various capsules to achieve good results. Instead, it is necessary to fulfil an appropriate set of parameters which go far beyond mere optimization of known prior art. These parameters include the careful grouping and selection of different perfume oils and providing them in different microcapsules. This opens up the perfumery palette of encapsulated fragrances, widening the encapsulated fragrance creation scope, allowing the encapsulated fragrance to smell less functional and providing the benefit of a more realistic or true fragrance bouquet. Also, the perception of the bouquet of perfume is maintained for a longer time through the use of the different microcapsules of the present invention.

The mixed or hybrid microcapsules of the invention described herein can be used as perfuming ingredients in consumer products of the home- or personal-care type. This result is highly surprising since the consumer products contain high amounts (typically more than 10% of their own weight) of specific type of surfactant/tensioactive/solvents and which are known to significantly diminish the stability and the performance of such capsules. The use of the microcapsules disclosed herein provides improved deposition of the perfume on the treated surface together with an improved stability in a chemically aggressive environment. In other word the use of the capsules in various applications provides unforeseeable advantages over the same use of other similar prior art capsules.

The present invention also relates to the use of such microcapsules in a consumer product that is in the form of a home- or personal-care product. Such products may be either a solid or a liquid product. According to a particular embodiment, liquid products are preferred. The expression "home- or personal-care" has here the usual meaning in the art, and in particular it includes products such as body-care, hair-care or home-care products. Examples of liquid products according to the invention may be selected from the group consisting of a shampoo or a hair conditioner, a liquid detergent, a fabric softener, a shower or bath mousse, oil or gel, a deodorant or an antiperspirant. Preferably, the liquid perfumed product is a shampoo, a liquid detergent, a deodorant or a fabric softener. Examples of solid products according to the invention may be selected from the group consisting of a soap bar, a powder detergent or an air-freshener. As detergent products, there are considered applications such as detergent compositions or cleaning products for washing up or for cleaning various surfaces, for example, intended for textiles, dishes or hard surfaces (floors, tiles, stone-floors, etc). Preferably, the surface is a textile or a hard surface.

Conveniently, the mixture of microcapsules may be used as such to perfume the consumer products. For example, the mixture may be directly added to a consumer product in an amount of 0.1-30 wt. %, e.g. resulting in a total perfume content of about 0.0333-10 wt. %. Preferably, a consumer product according to the invention comprises about 0.01 to 4 wt. %, or even 4.5%, of its own weight, in capsules as defined above and containing the perfume oil ingredients. Of course, the above concentration may be adapted according to the olfactive effect desired in each product.

In another embodiment, the mixture of microcapsules may be sprayed onto a dry, powdered product, such as a washing powder or powdered detergent, to impart the desired fragrancing thereto. In the area of laundry products, for example, it has long been recognized that providing fragrances at different time points during the laundering process is desirable. Combinations of perfume ingredients having different boiling points have been reported. WO 2011/094681 discloses that perfume ingredients having a boiling point greater than 250° C. are important for imparting signature characters because they are generally substantive on dry fabric while perfume ingredients with boiling points lower than 250° C. tend to partition out of water into air and generally provide scent bloom in the air.

In the present invention, it has surprisingly been found that a better perfuming effect can be achieved by grouping the perfume oil ingredients upon consideration of their odor threshold concentrations, rather than by boiling points. The odor threshold concentration of a chemical compound is determined in part by its shape, polarity, partial charges and molecular mass. For convenience, the threshold concentration is presented as the common logarithm of the threshold concentration, i.e., Log [Threshold] ("LogT"). It has been found that perfume oil ingredients having a LogT value greater than −2.5 need to be present at a higher quantity to be perceived than those having a LogT value lower than −2.5.

As anticipated above, for the sake of clarity, it is understood that by "perfume oil" it is meant a single perfuming compound or a mixture of several perfuming compounds. Moreover, the phrase "perfume oil that has a LogT greater/lower than −2.5" means that preferably at least 80% of individual compounds, more preferably each separate perfuming compound present in the perfume oil has a LogT greater/lower than −2.5.

It is worth also mentioning that by "perfuming compound" it is meant here a compound, which is used in a perfuming preparation or a composition to impart a hedonic effect. In other words such compound, to be considered as being a perfuming one, must be recognized by a person skilled in the art as being able to impart or modify in a positive or pleasant way the odor of a composition, and not just as having an odor.

As shown in FIGS. 1A and B, in a sample of 200 previously reported perfume compounds having a boiling point of 250° C. or greater (to as high as about 450° C.), and a Log P value greater than 2.5 (to as high as around 8—the data points marked by grey squares), more than half of them have a LogT value below −2.5. Similarly, among 200 previously reported perfuming compound having a boiling point 250° C. or lower to as low as 100° C. and a Log P value greater than 2.5 (data points marked by black triangles), more than half of them have a LogT value greater than −2.5. Log P is the common logarithm of estimated octanol-water partition coefficient, which is known as a measure of lipophilicity. Perfuming compound having a Log P greater than 2.5 are of particular interest as they can be easily encapsulated.

Figure 2A:
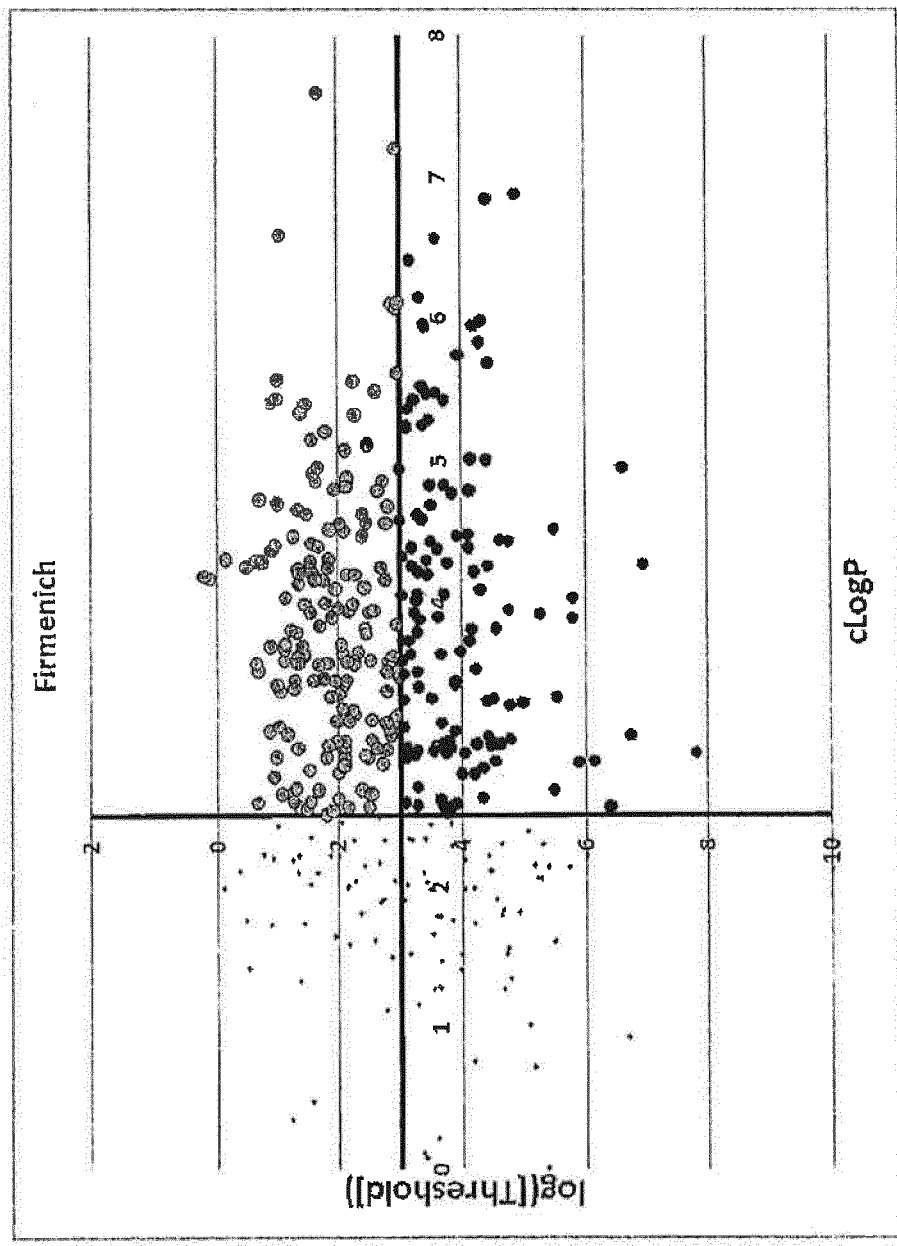
FIGS. 2A and B are graphs showing the odor threshold concentrations (A) and the boiling points (B) of the perfume oil ingredients used in the compositions of the invention.
Figure 2B:
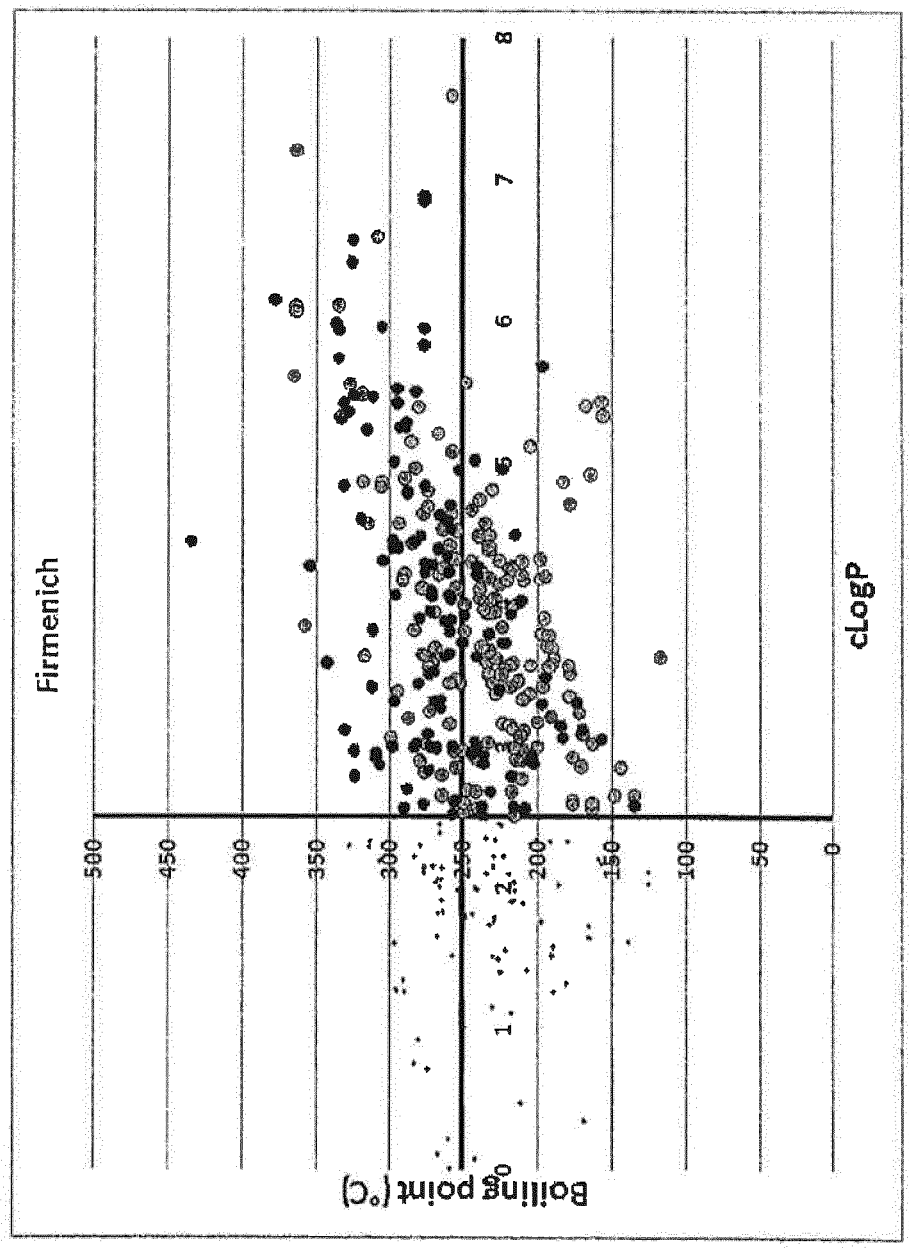

Conversely, as shown in FIGS. 2A and B, perfuming compound having a LogT value higher than −2.5 (data points marked by gray circles) have a similar boiling point distribution pattern as perfuming compound having a LogT value lower than −2.5 (data points marked by black circles). This result further confirms that there is no correlation between the boiling point and the odor threshold concentration of a perfuming compound.

In one embodiment, the invention provides a perfume composition comprising a first perfume microcapsule encapsulating a first perfume oil, which has a LogT greater than −2.5 and a cLogP greater than 2.5 and/or a volatility value of at least 30 μg/l air; and a second perfume microcapsule encapsulating a second perfume oil, which has a LogT less than −2.5 and a cLogP greater than 2.5 and/or a volatility value of at least 30 μg/l air.

The odor threshold concentration of a perfuming compound is determined by using a gas chromatograph ("GC"). Specifically, the gas chromatograph is calibrated to determine the exact volume of the perfume oil ingredient injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and hence the concentration of the perfuming compound. To determine the threshold concentration, solutions are delivered to the sniff port at the back-calculated concentration. A panelist sniffs the GC effluent and identifies the retention time when odor is noticed. The average across all panelists determines the odor threshold concentration of the perfuming compound. The determination of odor threshold is described in more detail in C. Vuilleumier et al., Multidimensional Visualization of Physical and Perceptual Data Leading to a Creative Approach in Fragrance Development, Perfume & Flavorist, Vol. 33, September, 2008, pages 54-61. Several examples are provided in U.S. Pat. No. 6,458,754 B1. The Log P values of many perfuming compound have been reported, for example, in the Pomona92 database, available from Daylight Chemical Information Systems, Inc. (Daylight CIS), Irvine, Calif., which also contains citations to the original literature. Log P values are most conveniently calculated by the "C LOG P" program, also available from Daylight CIS. This program also lists experimental log P values when they are available in the Pomona92 database. The "calculated log P" (cLogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each perfume oil ingredient, and takes into account the numbers and types of atoms, the atom connectivity, and chemical bonding. The cLogP values, which are the most reliable and widely used estimates for this physicochemical property, are preferably used instead of the experimental Log P values in the selection of perfuming compounds which are useful in the present invention.

Non-limiting examples of the perfuming compounds comprised in the first perfume oil are as follows:
2,6,10-Trimethyl-9-undecenal
2-propenyl hexanoate
cis-3-Hexenyl 2-methylbutanoate
decanal
Cis-3-Hexenyl-methyl-carbonate
nonanal
9-decen-1-ol
methyl-3-heptanone oxime
(2S,5R)-2-isopropyl-5-methylcyclohexanone
1,7,7-Trimethylbicyclo[2.2.1]heptan-2-one
para tert-butylcyclohexanone
isobornyl acetate
cyclohexyl 2-hydroxybenzoate
allyl cyclohexyl propionate
dihydroterpenyl acetate
2,4,6-trimethyl-4-phenyl-meta-dioxane
2-heptyl-1-cyclopentanone
(3,4-dihydroxyphenyl)acetate
Trimethyl cyclodecatrine epoxide
6 ethyl-3,10,10-trimethyl-4-oxaspiro[4.5]deca-1,6-diene
4-tert-butyl-cyclohexyl acetate.

Non-limiting examples of the perfuming compounds comprised in the second perfume oil are as follows:
1-(1-ethoxyethoxy)propane
Allyl (2-methylbutoxy)acetate
prop-2-enyl 2-(3-methylbutoxy)acetate
1-Octen-3-ol
trans-Anethole
3-(4-tert-Butylphenyl)propanal
2,6-Nonadien-1-ol
[(3,7-dimethyl-6-octenyl)oxy]-acetaldehyde
Lauronitrile
2,4-dimethyl-3-cyclohexene-1-carbaldehyde
1-(2,6,6-trimethyl-1,3-cyclohexadien-1-yl)-2-buten-1-one
1-(2,6,6-trimethyl-2-cydohexen-1-yl)-, (E)-2-buten-1-one
gamma-Decalactone
trans-4-decenal
2-Pentyl cyclopentanone
1-(2,6,6 Trimethyl-3-Cyclohexen-1-yl)-2-Buten-1-one)
1,1'-oxybis-benzene
1-(5,5-dimethyl-1-cyclohexen-1-yl-4-enten-1-one
Ethyl-2-methylbutanoate
1,3,3-trimethyl-2-oxabicyclo[2.2.2]octane
Eugenol
3-(3-isopropylphenyl)butanal
methyl 2-octynoate
4-(2,6,6-trimethyl-1-cyclohexen-1-yl-3-buten-2-one
2-methoxy-3-(2-methylpropyl)-pyrazine
Isobutyl quonoline
Isoeugenol
tetrahydro-6-(3-pentenyl)-2H-Pyran-2-one.

Figure 3A:
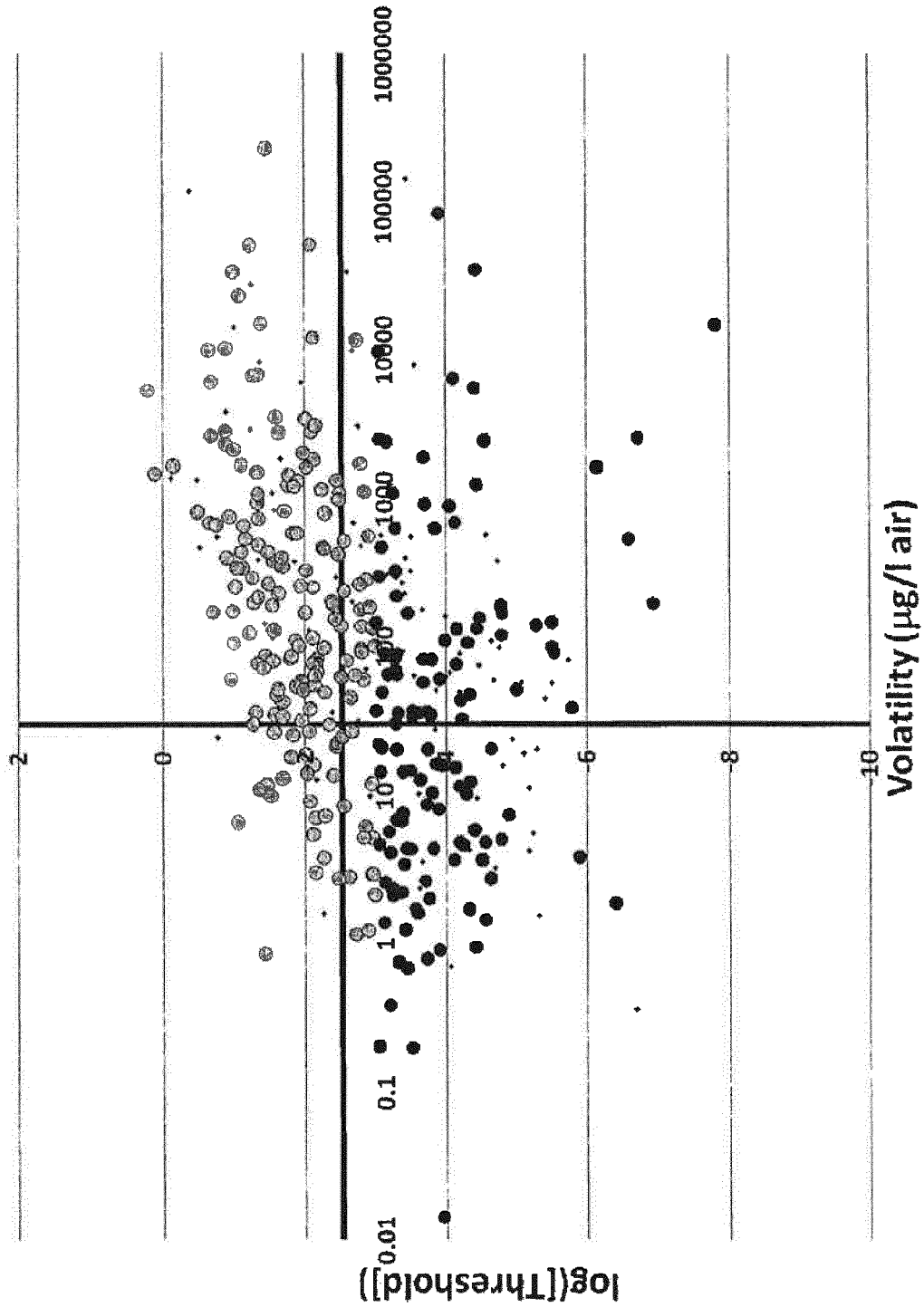
FIGS. 3A and B are graphs showing that odor threshold concentration is a crucial parameter for selecting perfume oil ingredients for encapsulation in different types of microcapsules (A) while boiling point does not correlate with suitable choices for encapsulation (B).
Figure 3B:
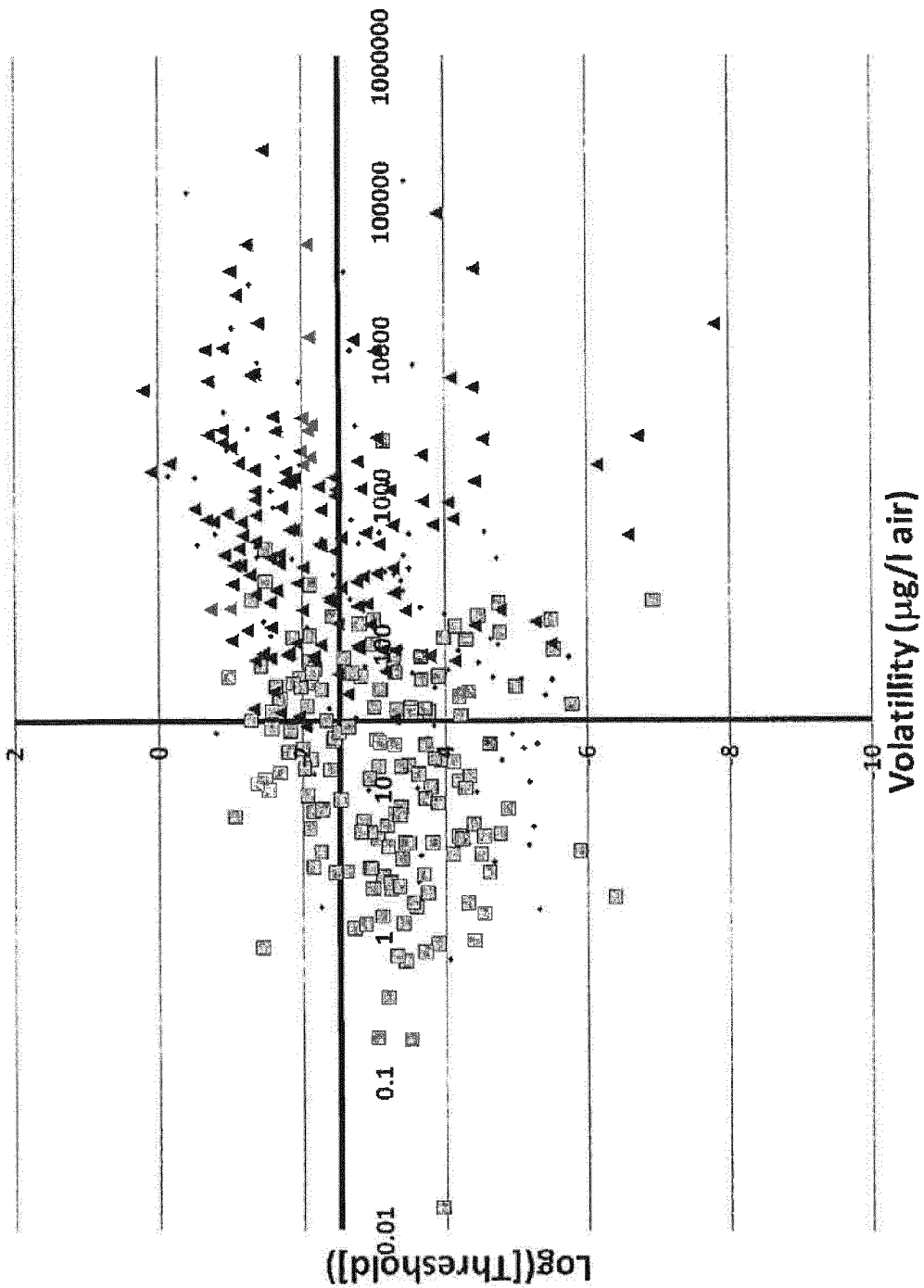

The determination of volatility values is described in more detail in C. Vuilleumier et al., Multidimensional Visualization of Physical and Perceptual Data Leading to a Creative Approach in Fragrance Development, Perfume & Flavorist, Vol. 33, September, 2008, pages 54-61. As shown in FIG. 3A, perfume oil ingredients having a log T higher than −2.5 and a volatility value greater than 30 μg/l air to as high as available (e.g., $5 \times 10^5$ g/l air) are preferably encapsulated in mechanical release capsules or in a more diffusive capsule (e.g., one with a less amount of monomer, or of a different monomer). In contrast, for a perfume oil ingredient having a LogT lower than −2.5 and lower volatilities (black circles), encapsulation is needed to enhance the stability of the raw materials in the base application, or to avoid degradation of the raw materials in the base. It is noted that the boiling points of the perfume oil ingredients, which correlate with the volatility values do not provide any information regarding suitable encapsulation choices (see FIG. 3B).

The perfume oil of the invention may comprise a single compound or a mixture of compounds. When a mixture of compounds is used, at least 80% of the compounds, preferably 90%, more preferably each compound in the mixture separately has a LogT and cLogP or volatility value in the ranges described herein. Preferably, at least 80% by weight of compounds that are encapsulated have the recited LogT and cLogPs or volatility values described herein, namely, the first perfume oil having a LogT greater than −2.5 and a Log P greater than 2.5 and/or a volatility value of at least 30 μg/l air, and the second perfume oil having a LogT less than −2.5 and a Log P greater than 2.5 and/or a volatility value of at least 30 μg/l air.

In a preferred embodiment of the invention, the first, second or both perfume microcapsule(s) have a core/shell structure, wherein the encapsulating material forms the shell while the perfume oil ingredients form the core.

For the preferred uses of the microcapsules in home care application in particular all purpose cleaners, fabric care application in particular fabric softening compositions, body care applications in particular deodorant compositions for example, various mixtures of microcapsules are desirable. For these embodiments, the first perfume microcapsules (i.e., those with the higher volatility perfuming oil ingredient) generally contain a first perfume oil wherein less than 50% by weight of its perfume oil compounds or constituents each has a boiling point of 250° C. or higher, and preferably 40% or less to as low as 1 to 5%. Also, the second perfume microcapsules (i.e., those with the lower volatility perfuming oil ingredient) contain generally contain a first perfume oil wherein more than 50% by weight of its perfume oil compounds or constituents each has a boiling point of 250° C. or lower, and preferably 60% or more to as much as 95 to 100%.

The foregoing combinations of microcapsules provide a highly desirable diffusion of the perfume oil ingredients from the formulation, It is also possible for the first perfume microcapsules to contain a lower amount of compound(s) having a boiling point of 250° C. or higher, such as 24 to 20% or less to as low as 1 to 5% by weight relative to the total oil, depending upon the particular perfuming oil ingredient that is encapsulated. Also, the second perfume microcapsules can contain compound(s) having a boiling point of 250° C. or lower in amounts of 65 to 80% by weight relative to the total oil, again depending upon the particular oil that is encapsulated. The skilled artisan having this disclosure before him or her can easily select the most desirable compounds or combination of compounds for any particular application by routine testing.

The relative amounts of the two types of capsules in a particular formulation can vary from 1 to 99% by weight of one type and 99 to 1% by weight of the other type. More specifically, the weight ratio of the two different microcapsules is between 5:1 and 1:5 and preferably is between 3:1 and 1:3. The perfumer can determine the best combinations by routine testing for any particular product that is to be perfumed. For example, in some situations, it may be desirable to have a greater scent upon opening of the product, while for others, the delayed release of the fragrance is desirable as it can be transferred to the person's body, a surface to be cleaned or a fabric to be laundered. And although the amounts of perfuming oil per weight in the capsules can be varied as described above for fabric care application in particular fabric softeners, home care applications in particular all purpose cleaner and body care applications in particular deodorants, it is also possible to use capsules that only contain the perfuming oil (i.e., that contain 100% by weight of the perfuming oil ingredient). In addition, the perfume oil may indeed contain from 0% to 50% of other constituents that are not perfuming compounds, such as solvents (e.g., diisopropyl glycol or isopropyl myristate), stabilizers such as BHT, etc., or other constituents which are typically included with such oils or constituents. Again, a skilled artisan can best determine what is needed for any particular application or formulation.

Another way to achieve a desirable release of the different perfuming oil would be to provide the first microcapsules with a thinner capsule wall than for the second microcapsules. When the resin type is the same, the use of less monomer for preparing the microcapsule resin generally provides thinner wall capsules. A higher amount of the monomer creates a less permeating barrier, while a lower amount provides a barrier that is permeated more easily. Yet another way would be to vary the monomer type of the two microcapsules. For example, aromatic isocyanate TAKENATE® monomers provide a less permeating bather while aliphatic isocyanate, DESMODUR® monomers provide a more permeating barrier. In addition, the perfume oil can be encapsulated in different ways to achieve this difference, such as by solid wall encapsulation (for a greater barrier effect) compared to matrix encapsulation (for a lesser barrier effect). The skilled artisan can select these different features by routine testing depending upon the specific perfume oil ingredients to be included in the mixtures.

Thus, when a greater rate of diffusion is provided by the microcapsules that contain the first perfume oil, fragrances are perceived when initially handling the product, i.e., opening the bottle or package or when handling products that contain a mixture of the microcapsules. Thereafter, the less permeable microcapsules prevent the release of the second perfuming oil until a later time, such as when the product is used, e.g., as a detergent or fabric softener in the washing machine to transfer the perfuming oil onto the fabrics being washed, or in a cleaning product when the product is applied to clean a floor, or to a personal care product when it is used by the person.

In one embodiment of the invention, the perfume microcapsules encapsulating the first and the second perfume oil has a core/shell structure, wherein the encapsulating material forms the shell while the perfume oil forms the core.

The encapsulation of the perfume compositions may be carried out in a variety of means that are known to skilled artisans. Preferably, the perfume oil ingredients of the invention are encapsulated in a shell. The shell of the microcapsule for the respective first and second perfume microcapsules may be the same or different. Suitable perfume oil microcapsules may include those described in US patent application publication nos. 2003/0215417; 2003/0216488;

2003/0158344; 2003/0165692; 2004/0071742; 2004/0071746; 2004/0072719; 2004/0072720; 2003/0203829; 2003/0195133; 2004/0087477; 2004/00106536; 2008/00305982; and 2009/00247449; and in U.S. Pat. Nos. 7,119,057; 6,645,479; 6,200,949; 5,145,842; 4,917,920; 4,882,220; 4,514,461; 4,234,627; 4,081,384.

In one embodiment, the shell comprises an aminoplast copolymer, such as melamine-formaldehyde or urea-formaldehyde or cross-linked melamine formaldehyde or melamine glyoxal, or polyurea made from, for example but not limited to isocyanate-based monomers and amine-containing crosslinkers such as guanidine carbonate or guanazole, or polyurethane shells made from, for example but not limited to polyisocyanate and polyols, polyamide, polyester, etc. Preferred polyurea microcapsules comprise a polyurea wall which is the reaction product of the polymerisation between at least one polyisocyanate comprising at least two isocyanate functional groups and at least one reactant selected from the group consisting of a water soluble guanidine salt and guanidine; a colloidal stabilizer; and an encapsulated perfume. The colloidal stabilizer is an aqueous solution of between 0.1% and 0.4% of polyvinyl alcohol, between 0.6% and 1% of a cationic copolymer of vinylpyrrolidone and of a quaternized vinylimidazol (all percentages being defined by weight relative to the total weight of the colloidal stabilizer). Methods of making such polyurea microcapsules are described in U.S. patent application Ser. No. 12/993,190 filed Jun. 8, 2009, the entire content of which is expressly incorporated herein by reference thereto.

In another embodiment, the microcapsule comprises a wall material that surrounds the perfume oil. The skilled artisan is able to modify the release properties of the microcapsules by a variety of ways. The permeability of the wall can be varied by utilizing different types of resins or monomers, different amounts of such materials, or by different wall thicknesses of the same materials. The skilled artisan having this disclosure before him or her can easily select the most microcapsule structures and permeabilities for any particular application by routine testing.

In one aspect, at least 75%, 85% or even 90% of said microcapsules may have a particle size of from about 1 micron to about 100 microns, about 5 microns to 80 microns, from about 5 microns to about 50 microns, or even from about 5 microns to about 40 microns. In another aspect, at least 75%, 85% or even 90% of the microcapsules may have a particle wall thickness of from about 10 nm to about 250 nm, from about 30 nm to about 180 nm, or even from about 40 nm to about 120 nm.

In one aspect, said microcapsule wall material may comprise any suitable resin and especially including melamine, glyoxal, polyurea, polyurethane, polyamide, polyester, etc. Preferred resins include the reaction product of an aldehyde and an amine, suitable aldehydes include, formaldehyde. Suitable amines include melamine, urea, benzoguanamine, glycoluril, and mixtures thereof. Suitable melamines include, methylol melamine, methylated methylol melamine, imino melamine and mixtures thereof. Suitableureas include, dimethylol urea, methylated dimethylol urea, urea-resorcinol, and mixtures thereof. Suitable materials for making may be obtained from one or more of the following companies Solutia Inc. (St Louis, Miss. U.S.A.), Cytec Industries (West Paterson, N.J. U.S.A.), Sigma-Aldrich (St. Louis, Miss. U.S.A.). It has been found that it is possible to prepare microcapsules comprising a melamine-formaldehyde aminoplast co-polymer or ter-polymer containing polyol moieties, and especially aromatic polyol moieties. There are therefore provided microcapsules comprising a core of perfume, and a shell of aminoplast polymer, the composition of the shell being from 75-100% of a thermoset resin comprising 50-90%, preferably from 60-85%, of a co-polymer and from 10-50%, preferably from 10-25%, of a polymeric stabilizer; the co-polymer comprising: (a) from 20-60%, preferably 30-50% of moieties derived from at least one polyamine, (b) from 3-50%, preferably 5-25% of moieties derived from at least one aromatic polyol; and (c) from 20-70%, preferably 40-60% of moieties selected from the group consisting of alkylene and alkylenoxy moieties having 1 to 6 methylene units, preferably 1 to 4 methylene units and most preferably a methylene unit, dimethoxy methylene and dimethoxy methylene.

By "moiety" is meant a chemical entity, which is part of the polymer and which is derived from a particular molecule. Example of suitable polyamine moieties include, but are not limited to, those derived from urea, melamine, 3-substituted 1,5-30 diamino-2,4,6-triazin and glycouril. Examples of suitable aromatic polyol moieties include, but are not limited to, those derived from phenol, 3,5-dihydroxy toluene, Bisphenol A, resorcinol, hydroquinone, xylenol, polyhydroxy naphthalene and polyphenols produced by the degradation of cellulose and humic acids.

The use of the term "derived from" does not necessarily mean that the moiety in the co-polymer is directly derived from the substance itself, although this may be (and often is) the case. In fact, one of the more convenient methods of preparing the co-polymer involves the use of alkylolated polyamines as starting materials; these combine in a single molecule both the moieties (a) and (c) mentioned hereinabove. Suitable alkylolated polyamines encompass mixtures of mono- or polyalkylolated polyamines, which in turn may be partially alkylated with alcohols having from 1 to 6 methylene units. Alkylated polyamines especially suitable for the sake of the present invention include mono- and polymethylol-urea pre-condensates, such as those commercially available under the trademark URAC® (from Cytec Technology Corp.) and/or partially methylated mono- and polymethylol-1,3,5-triamino-2,4,6-triazine pre-condensates, such as those commercially available under the trademark CYMEL® (from Cytec Technology Corp.) or LURACOLL® (from BASF), and/or mono- and polyalkylol-benzoguanamine pre-condensates, and/or mono- and polyalkylol-glycouril pre-condensates. These alkylolated polyamines may be provided in partially alkylated forms, obtained by addition of short chain alcohols having typically 1 to 6 methylene units. These partially alkylated forms are known to be less reactive and therefore more stable during storage. Preferred polyalkylol-polyamines are polymethylol-melamines and polymethylol-1-(3,5-dihydroxy-methylbenzyl)-3,5-triamino-2,4,6-triazine.

A polymeric stabilizer may be used to prevent the microcapsules from agglomerating, thus acting as a protective colloid. It is added to the monomer mixture prior to polymerisation, and this results in its being partially retained by the polymer. Particular examples of suitable polymeric stabilizers include acrylic copolymers bearing sulfonate groups, such as those available commercially under the trademark LUPASOL® (from BASF), such as LUPASOL® PA 140 or LUPASOL® VFR; copolymers of acrylamide and acrylic acid, copolymers of alkyl acrylates and N-vinylpyrrolidone, such as those available under the trademark LUVISKOL® (e.g., LUVISKOL® K 15, K 30 or K 90 from BASF); sodium polycarboxylates (from Polyscience Inc.) or sodium poly(styrene sulfonate) (from Polyscience Inc.); vinyl and methyl vinyl ether-maleic anhydride copolymers (e.g. AGRIMER® #8482 or VEMA® #8482), and ethylene, isobutylene or styrene-maleic anhydride copolymers. Hence the preferred polymer stabilizers are anionic polyelectrolytes.

Microcapsules of the type hereinabove described are manufactured in the form of an aqueous slurry, having typically 20 to 50% solids content, and more typically 30 to 45% solid content, where the term "solids content" refers to the total weight of the microcapsules. The slurry may contain formulation aids, such as stabilizing and viscosity control hydrocolloids, biocides, and additional formaldehyde scavengers.

Typically, hydrocolloids or emulsifiers are used during the emulsification process of a perfume. Such colloids improve the stability of the slurry against coagulation, sedimentation and creaming. The term "hydrocolloid" refers to a broad class of water-soluble or water-dispersible polymers having anionic, cationic, zwitterionic or non-ionic character. These hydrocolloids or emulsifiers may comprise a moiety selected from the group consisting of carboxy, hydroxyl, thiol, amine, amide and combination thereof. Hydrocolloids useful for the sake of the present invention encompass: polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-comaleic acid)copolymer, poly(alkyleneoxide), poly(vinylmethyl ether), poly(vinylether-co-maleic anhydride), and the like, as well as poly-(ethylene imine), poly((meth)acrylamide), poly(alkyleneoxide-co-dimethylsiloxane), poly(amino dimethylsiloxane), and the like, and their quaternized forms. In one aspect, said emulsifier may have a pKa of less than 5, preferably greater than 0, but less than 5. Emulsifiers include acrylic acid-alkyl acrylate copolymers, poly(acrylic acid), polyoxyalkylene sorbitan fatty esters, polyalkylene co-carboxy anhydrides, poly alkylen co-maleic anhydrides, poly (methyl vinyl ether-co-maleic anhydride), poly(butadiene co-maleic anhydride), and poly(vinyl acetate-co-maleic anhydride), polyvinyl alcohols, polyalkylene glycols, polyoxyalkylene glycols and mixtures thereof. Most preferably the hydrocolloid is poly acrylic acid or modified poly acrylic acid. The pKa of the colloids is preferably between 4 and 5, and hence the capsule has a negative charge when the PMC slurry has pH above 5.0.

The microcapsules preferably comprise a nominal shell to core mass ratio lower than 15%, preferably lower than 10% and most preferably lower than 5%. Hence, the microcapsules may have extremely thin and frangible shells. The shell to core ratio is obtained by measuring the effective amount of encapsulated perfume microcapsules that have been previously washed with water and separated by filtration. This is achieved by extracting the wet microcapsule cake by microwave-enhanced solvent extraction and subsequent gas chromatographic analysis of the extract.

Preferably, the perfume is encapsulated within a resin capsule of any of the types mentioned herein. For an aminoplast capsule, for example, the capsule shell comprises a urea-formaldehyde or melamine-formaldehyde polymer. More preferably, the microcapsule is further coated or partially coated in a second polymer comprising a polymer or copolymer of one or more anhydrides (such as maleic anhydride or ethylene/maleic anhydride copolymer).

The microcapsules of the present invention may be positively or negatively charged. It is preferred that the microcapsules of the present invention are negatively charged, however, and have a zeta potential of from −0.1 meV to −100 meV, when dispersed in deionized water. By "zeta potential" (z) it is meant the apparent electrostatic potential generated by any electrically charged objects in solution, as measured by specific measurement techniques. The zeta potential of an object is measured at some distance from the surface of the object and is generally not equal to and lower than the electrostatic potential at the surface itself. Nevertheless, its value provides a suitable measure of the capability of the object to establish electrostatic interactions with other objects present in the solution, especially with molecules with multiple binding sites. The zeta-potential is a relative measurement and its value depends on the way it is measured. In the present case, the zeta-potential of the microcapsules is measured by the so-called phase analysis light scattering method, using a Malvern Zetasizer equipment (Malvern Zetasizer 3000; Malvern Instruments Ltd; Worcestershire UK, WR14 lXZ). The zeta potential of a given object may also depend on the quantity of ions present in the solution. The values of the zeta-potential specified in the present application are measured in deionized water, where only the counter-ions of the charged microcapsules are present. More preferably the microcapsules of the present invention have zeta potential of −10 meV to −80 meV, and most preferred from −20 meV to −75 meV.

Processes for making microcapsules are described in the art, such as those disclosed in U.S. Pat. Nos. 6,592,990 and 6,544,926. The composition resulting from this manufacturing process is a slurry. The slurry comprises microcapsules, water and precursor materials for making the microcapsules. The slurry may comprise other minor ingredients, such as an activator for the polymerization process and/or a pH buffer. To the slurry, a formaldehyde scavenger may be added.

The perfume composition of the present invention may comprise other ingredients selected from the list of optional ingredients set out below. Unless specified herein below, an "effective amount" of a particular laundry adjunct is preferably from 0.01%, more preferably from 0.1%, even more preferably from 1% to 20%, more preferably to 15%, even more preferably to 10%, still even more preferably to 7%, most preferably to 5% by weight of the detergent compositions.

Ionic Species

The compositions of the present invention preferably comprise an ionic species having at least 2 anionic sites. The ionic species is further believed in some instances to be aided by an interaction with cations and ions in the composition.

In one aspect of the invention, the ionic species is selected from the group consisting of carboxylic acids, polycarboxylate, phosphate, phosphonate, polyphosphate, polyphosphonate, borate and mixtures thereof, having 2 or more anionic sites.

In one aspect, the ionic species is selected from the group consisting of oxydisuccinic acid, aconitic acid, citric acid, tartaric acid, malic acid, maleic acid, fumaric acid, succinic acid, sepacic acid, citaconic acid, adipic acid, itaconic acid, dodecanoic acid and mixtures thereof.

In a further aspect of the present invention, the composition comprises an ionic species is selected from the group consisting of acrylic acid homopolymers and copolymers of acrylic acid and maleic acid and mixtures thereof.

In a preferred aspect of the present invention, the composition comprises positively charged ions comprising at least 2 cationic sites. In one aspect of the invention, the positively charged ion is selected from calcium, magnesium, iron, manganese, cobalt, copper, zinc ions and mixtures thereof.

The ionic species having at least 2 anionic sites are present in the composition such that they provide an ionic strength of greater than 0.045 mol/kg. More preferably the ionic strength delivered by the ionic species having at least 2 anionic sites is from 0.05 to 2 mol/kg, most preferably from 0.07 to 0.5 mol/kg. Ionic strength is calculated by the equation:

$$\text{Ionic Strength} = \tfrac{1}{2}\sqrt{(C_i Z_i^2)}$$

where $C_i$=concentration of ionic species in finished product (mol/kg), z is the charge for the ionic species.

Formaldehyde Scavenger

The compositions of the present invention preferably comprise a formaldehyde scavenger. The formaldehyde scavengers are preferably selected from the group consisting of acetoacetamide, ammonium hydroxide, alkali or alkali earth metal sulfite, bisulfite and mixtures thereof. Most preferably the formaldehyde scavenger is a combination of potassium sulfite and acetoacetamide. The formaldehyde scavenger according to the present invention is present at a total level of from 0.001% to about 3.0%, more preferably from about 0.01% to about 1%.

Pearlescent Agent

In one embodiment of the present invention, the composition may comprise a pearlescent agent. Preferred inorganic pearlescent agents include those selected from the group consisting of mica, metal oxide coated mica, silica coated mica, bismuth oxychloride coated mica, bismuth oxychloride, myristyl myristate, glass, metal oxide coated glass, guanine, glitter (polyester or metallic) and mixtures thereof.

Benefit Agents

The compositions of the present invention may comprise a benefit agents. As used herein, "benefit agent" refers to any material that can provide benefits to the surface or fabric to which it is applied. AS an example, fabric care benefits include fabric softening, color protection, pill/fuzz reduction, anti-abrasion, antiwrinkle, and the like to garments and fabrics, particularly on cotton and cotton-rich garments and fabrics, when an adequate amount of the material is present on the garment/fabric. Non-limiting examples of such benefit agents include cationic surfactants, silicones, polyolefin waxes, latexes, oily sugar derivatives, cationic polysaccharides, polyurethanes, fatty acids and mixtures thereof.

Detersive Enzymes

Suitable detersive enzymes for optional use herein include protease, amylase, lipase, cellulase, carbohydrase including mannanase and endoglucanase, and mixtures thereof. Enzymes can be used at their art-taught levels, for example at levels recommended by suppliers such as Novo and Genencor. Typical levels in the compositions are from about 0.0001% to about 5%. When enzymes are present, they can be used at very low levels, e.g., from about 0.001% or lower, in certain embodiments of the invention; or they can be used in heavier-duty laundry detergent formulations in accordance with the invention at higher levels, e.g., about 0.1% and higher. In accordance with a preference of some consumers for "non-biological" detergents, the present invention includes both enzyme-containing and enzyme-free embodiments.

Deposition Aid

As used herein, "deposition aid" refers to any cationic or amphoteric polymer or combination of cationic and amphoteric polymers that significantly enhance the deposition of the fabric care benefit agent onto the fabric during laundering or in other applications where the perfume oil ingredient is to be transferred to a surface or fabric. Preferably, the deposition aid, where present, is a cationic or amphoteric polymer.

Rheology Modifier

In a preferred embodiment of the present invention, the composition comprises a rheology modifier. Generally the rheology modifier will comprise from 0.01% to 1% by weight, preferably from 0.05% to 0.75% by weight, more preferably from 0.1% to 0.5% by weight, of the compositions herein. Preferred rheology modifiers include crystalline, hydroxyl-containing rheology modifiers include castor oil and its derivatives, polyacrylate, pectin, alginate, arabinogalactan (gum Arabic), carrageenan, gellan gum, xanthan gum, guar gum and mixtures thereof.

Builder

The compositions of the present invention may optionally comprise a builder. Suitable builders include polycarboxylate builders, citrate builders, nitrogen-containing, phosphor-free aminocarboxylates include ethylene diamine disuccinic acid and salts thereof (ethylene diamine disuccinates, EDDS), ethylene diamine tetraacetic acid and salts thereof (ethylene diamine tetraacetates, EDTA), and diethylene triamine penta acetic acid and salts thereof (diethylene triamine penta acetates, DTPA) and water-soluble salts of homo- and copolymers of aliphatic carboxylic acids such as maleic acid, itaconic acid, mesaconic acid, fumaric acid, aconitic acid, citraconic acid and methylenemalonic acid.

The perfume composition of the invention are useful in consumer products where perfume releases at different time points are desirable. In a preferred embodiment, the invention provides a laundry and cleaning composition comprising the perfume composition of the invention and a detersive ingredient. Preferably, the laundry and cleaning composition is selected from the group consisting of a detergent composition, a hard surface cleaning composition, and a dishwashing composition. The invention also provides a process for making such laundry and cleaning composition, which comprises the step of combining the perfume composition of the invention, by means selected from spraying, dry-mixing, and mixtures thereof, with the detersive ingredient.

Most preferably, the laundry and cleaning composition is a fabric detergent or softener composition. Typical examples of fabric detergent or softener composition into which the perfuming composition of the invention can be incorporated are described in WO 97/34986 or in U.S. Pat. Nos. 4,137,180 and 5,236,615 or EP 799,885. Other typical detergent and softening compositions which can be used are described in works such as Ullman's Encyclopedia of Industrial Chemistry, vol. A8, pages 315-448 (1987) and vol. A25, pages 747-817 (1994); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

Another advantage of the invention is that the preparation mixtures of microcapsules as disclosed herein results in beneficial effects on the retention of the perfume oil ingredients in the microcapsules over time. Thus, the aging process of the microcapsules is reduced, such that the microcapsules or products containing them can be stored over time for longer periods compared to other formulations of microcapsules that are not prepared as noted herein. Thus, the present invention increases the shelf life of home- or personal-care products that contains these mixtures of microcapsules.

Capsules Performance

The performance of the present microcapsules can be determined by olfactive evaluations and measurements (see Example 1), as well as by analytical methods (headspace) (see Examples 2-4).

In the case of olfactive evaluations, the measurement process starts with the determination of the intensity of a perfuming oil smelled by the panelists (this is called perceived intensity). This is done in a session wherein the panelists rate the intensity of the studied ingredient at four different concentrations chosen between its volatility value and $10^{-6}$ µg/l air, which corresponds to a low threshold value. The ratings for these four initial concentration steps serve as the basis for the choice of the next four concentration levels used in a second experiment, and thus span the supraliminal concentration domain where intensity changes noticeably with concentration. We then fit the experimental points to a sigmoidal curve using a non-linear regression of the following form:

$$\text{Intensity} = IMax \frac{1}{1 + (\text{Exp}(-CurveParameterI \cdot (\text{LOG}(Conc.) - TetaI)))}$$

A sigmoidal curve is defined by 3 parameters. These are Imax (the asymptotic value for the perceived intensity), TetaI (the logarithmic value of gaseous concentration corresponding to the inflexion point of the curve) and the Curve ParameterI. This last one is related to the tangent value, SlopeI, at the TetaI concentration by the following equation:

$$SlopeI = \frac{CurveParameterI \cdot IMax}{4}$$

A steep slope may suggest that the perfumery ingredient is more sensitive to the applied dosage in a fragrance, which leads to a rapid decrease of intensity if the concentration falls. A decrease in concentration is typically the situation for fragrance loss during washing, rinsing and drying operations for laundry or body-care products. The Dose-Response curves are useful for the prediction of a perceived intensity based on a gas phase concentration.

EXAMPLES

The following non-limiting examples are illustrative of the present invention.

Example 1

Benchmark Microcapsules
Composition of the oil:

| Ingredient | Amount (%) | clogP | Boiling point (° C.) |
|---|---|---|---|
| Camphor | 2.62 | 2.50 | 204 |
| Menthone | 1.57 | 3.46 | 213 |
| Methylhexylketone | 0.21 | 2.60 | 164 |

-continued

| Ingredient | Amount (%) | clogP | Boiling point (° C.) |
|---|---|---|---|
| Isobornyle acetate | 10.48 | 4.13 | 226 |
| Linalyl acetate | 2.10 | 4.04 | 229 |
| Terpenyl acetate | 5.24 | 4.73 | 239 |
| Dihydromyrcenol | 10.48 | 3.21 | 191 |
| cis-2-methyl-4-propyl-1,3-oxathiane | 0.10 | 2.35 | 209 |
| Aldehyde MNA | 3.14 | 5.01 | 242 |
| Allyl amyl glycolate | 2.10 | 2.79 | 218 |
| delta Damascone | 0.52 | 4.13 | 192 |
| Eucalyptol | 5.24 | 3.31 | 174 |
| allyl (cyclohexyloxy)-acetate | 1.05 | 2.62 | 255 |
| Methyl ionones | 2.10 | 4.83 | 276 |
| neobutenone® [1] alpha | 1.05 | 3.89 | 258 |
| 2,4-Dimethyl-3-cyclohexene-1-carbaldehyde | 1.05 | 2.34 | 200 |
| Cetalox® [2] | 0.52 | 5.83 | 277 |
| ISO® [3] E Super | 10.48 | 5.24 | 294 |
| Lilial® [4] | 15.72 | 3.90 | 280 |
| Methylnaphtylketone | 0.52 | 2.50 | 297 |
| Hedione® [5] | 5.24 | 2.92 | 309 |
| Crystal moss | 0.10 | 3.22 | 328 |
| Habanolide® [6] | 4.19 | 5.61 | 366 |
| Cashmeran® [7] | 2.10 | 3.65 | 278 |
| Cedrenol | 1.57 | 4.33 | 280 |

[1] 1-(5,5-dimethyl-1-cyclohexen-1-yl)-4-penten-1-one; origin: Firmenich SA
[2] dodecahydro-3a,6,6,9a-tetramethyl-naphtho[2,1-b]furan; origin: Firmenich SA
[3] 1-(octahydro-2,3,8,8-tetramethyl-2-naphtalenyl)-1-ethanone; origin: International Flavors & Fragrances, USA
[4] 3-(4-tert-butylphenyl)-2-methylpropanal; origin: Givaudan SA, Vernier, Switzerland
[5] Methyl dihydrojasmonate; origin: Firmenich SA
[6] pentadecenolide; origin: Firmenich SA
[7] 1,2,3,5,6,7-hexahydro-1,1,2,3,3-pentamethyl-4-indenone; origin: International Flavors & Fragrances, USA Making Benchmark Microcapsules All the ingredients from the oil were encapsulated in the same capsule, regardless of the ODT values.

4.38 g of TAKENATE® D 110N (from Mitsui Chemicals) was dissolved in 40 g of the perfume oil described above. This oil phase was introduced in a 150 mL beaker equipped with a scrapped stirrer and an Ika-rotor/stator system (6500-24000 rpm). The oil phase was stirred at 50 rpm with the scrapped stirrer for 5 minutes.

An aqueous stabilizer solution at 1% by weight, relative to the total weight of the stabilizer solution, was prepared by dissolving the polyvinyl alcohol (MOWIOL® 18-88 from Fluka) in 50.8 g of deionised water.

An emulsion was then prepared by homogenizing the perfume phase in the aqueous phase with the Ika-digital Ultra-Turax system during 3 minutes at 24000 rpm. The resulting emulsion solution was introduced into a 100 mL reactor at room temperature and the stirring was set at 500 rpm.

Then, a solution of the 0.90 g of guanidine carbonate in 2.7 g of deionised water was added to the reactor over one hour at room temperature. The reaction temperature was elevated to 50° C. over 30 minutes, to 70° C. over the next 30 minutes and was maintained at 70° C. for the next 2 hours. The reaction was cooled down to room temperature for 30 minutes.

In this batch, 12 mmol of isocyanate and 20 mmol of amine were used as the resin to encapsulate 40 g of oil. With this composition, compounds with high ODT are present in the headspace at too high of a quantity which causes an over-powering note, and the compounds with low ODT are not present in the headspace at a sufficient amount and thus not perceivable.

Capsules According to the Invention
First Microcapsules:
Composition of the first perfuming oil (log T>−2.5):

| Perfuming compound | Amount (%) | clogP | Boiling point (° C.) |
|---|---|---|---|
| Camphor | 7.6 | 2.50 | 204 |
| Menthone | 4.6 | 3.46 | 213 |
| Methylhexylketone | 0.6 | 2.60 | 164 |
| Isobornyle acetate | 30.5 | 4.13 | 226 |
| Linalyl acetate | 6.1 | 4.04 | 229 |
| Terpenyl acetate | 15.2 | 4.73 | 239 |
| Dihydromyrcenol | 30.5 | 3.21 | 191 |
| cis-2-methyl-4-propyl-1,3-oxathiane | 0.3 | 2.35 | 209 |

Making of the First Microcapsules 1.15 g of DESMODUR® N 100 was dissolved in 40 g of the first perfume oil. This oil phase was introduced in a 150 mL beaker equipped with a scrapped stirrer and an Ika-rotor/stator system (6500-24000 rpm). The oil phase was stirred at 50 rpm with the scrapped stirrer for 5 minutes.

An aqueous stabilizer solution at 1% by weight, relative to the total weight of the stabilizer solution, was prepared by dissolving the polyvinyl alcohol (MOWIOL® 18-88) in 50.8 g of deionised water.

An emulsion was then prepared by homogenizing the perfume phase in the aqueous phase with the Ika-digital Ultra-Turax system during 3 minutes at 24000 rpm. The resulting emulsion solution was introduced into a 100 mL reactor at room temperature and the stirring was set at 500 rpm.

Then, a solution of the 0.45 g of guanidine carbonate in 2.7 g of deionised water was added to the reactor over one hour at room temperature. The reaction temperature was elevated to 50° C. over 30 minutes, to 70° C. over the next 30 minutes and was maintained at 70° C. for the next 2 hours. The reaction was cooled down to room temperature for 30 minutes The capsule was made with 6 mmol (1.15 g) of isocyanate and 10 mmol (0.45 g) of amine to encapsulate 40 g of oil. The resin to oil weight ratio is therefore 1:25.

Second Microcapsules:
Composition of the second perfume oil (log T<−2.5)

| Perfuming compound | Amount (%) | clogP | Boiling point (° C.) |
|---|---|---|---|
| Aldehyde MNA | 19.1 | 5.01 | 242 |
| Allyl amyl glycolate | 12.7 | 2.79 | 218 |
| delta Damascone | 3.2 | 4.13 | 192 |
| Eucalyptol | 31.8 | 3.31 | 174 |
| allyl (cyclohexyloxy)-acetate | 6.4 | 2.62 | 255 |
| Methyl ionones | 12.7 | 4.83 | 276 |
| neobutenone® alpha | 6.4 | 3.89 | 258 |
| 2,4-Dimethyl-3-cyclohexene-1-carbaldehyde | 6.4 | 2.34 | 200 |

Making of the Second Microcapsules 2.29 g DESMODUR® N 100 was dissolved in 40 g of the second perfume oil. This oil phase was introduced in a 150 mL beaker equipped with a scrapped stirrer and an Ika-rotor/stator system (6500-24000 rpm). The oil phase was stirred at 50 rpm with the scrapped stirrer for 5 minutes.

An aqueous stabilizer solution at 1% by weight, relative to the total weight of the stabilizer solution, was prepared by dissolving the polyvinyl alcohol in 50.8 g of deionised water.

An emulsion was then prepared by homogenizing the perfume phase in the aqueous phase with the Ika-digital Ultra-Turax system during 3 minutes at 24000 rpm. The resulting emulsion solution was introduced into a 100 mL reactor at room temperature and the stirring was set at 500 rpm.

Then, 0.9 g of the guanidine carbonate in 5.4 g of deionised water was added to the reactor over one hour at room temperature. The reaction temperature was elevated to 50° C. over 30 minutes, to 70° C. over the next 30 minutes and was maintained at 70° C. for the next 2 hours. The reaction was cooled down to room temperature for 30 minutes.

The perfume content in the capsules suspension was around 40%, relative to the total weight of the suspension. The capsule was made with 12 mmol (2.29 g) of isocyanate and 20 mmol (0.90 g) of amine to encapsulate 40 g of oil. The resin to oil weight ratio is therefore 1:12.5.

Free Perfume Oil:
Composition of the third perfuming oil

| Ingredient | Amount (%) | clogP | Boiling point (° C.) |
|---|---|---|---|
| Cetalox ® | 1.2 | 5.83 | 277 |
| ISO ® E Super | 24.0 | 5.24 | 294 |
| Lilial ® | 36.1 | 3.90 | 280 |
| Methylnaphtylketone | 1.2 | 2.50 | 297 |
| Hedione ® | 12.0 | 2.92 | 309 |
| Mousse Crystal moss | 0.2 | 3.22 | 328 |
| Habanolide ® | 9.6 | 5.61 | 366 |
| Cashmeran ® | 4.8 | 3.65 | 278 |
| Cedrenol | 3.6 | 4.33 | 280 |

An emulsion of the third perfume oil was prepared by homogenizing the oil in the polyvinyl alcohol solution with the Ika-digital Ultra-Turax system for 3 minutes at 24000 rpm.

Mixture of Capsules According to the Invention and Free Perfume Oil

Batches containing the first and second capsule and the third perfume oil were mixed at a ratio of 3.5:2.2:4.3, which at the end provide in total the same perfuming composition as the benchmark capsule.

Results

The headspace samples of the deposited capsules were collected at the 24 hour time point and the concentrations were analyzed using the GC-MS. The GC column temperature setting was: 2 min 80° C. initial isothermal, then temperature program 3° C./min to 180° C., followed by a 10° C./min ramp to 250° C. The perceived intensity values were computed/correlated from the headspace concentrations measured using the equation described above.

Table 1 shows an increase in all of the Perfumery Raw Materials (PRMs) perceived intensity values before and after the perfumery raw materials were grouped. The perceived intensity (PI) is from a scale of 0 to 6. The invention accommodates a novel parameter to modulate the amounts of PRMs to be smelled in the headspace.

TABLE 1

Perceived Intensity Values

| Perfumery Raw Material | Benchmark | Invention | Δ Perceived Intensity |
|---|---|---|---|
| Methylhexylketone | 2.41 | 3.01 | 0.60 |
| Eucalyptol | 3.47 | 4.37 | 0.90 |
| Dihydromyrcenol | 4.44 | 4.50 | 0.06 |
| 2,4-Dimethyl-3-cyclohexene-1-carbaldehyde | 4.40 | 4.75 | 0.35 |

TABLE 1-continued

Perceived Intensity Values

| Perfumery Raw Material | Benchmark | Invention | Δ Perceived Intensity |
|---|---|---|---|
| Camphor | 2.61 | 5.45 | 2.84 |
| Methone | 3.97 | 4.65 | 0.68 |
| cis-2-methyl-4-propyl-1,3-oxathiane | 3.38 | 4.84 | 1.46 |
| Dihydromyrcenyl acetate | 1.47 | 4.05 | 2.58 |
| Allyl amyl glycolate | 3.07 | 3.14 | 0.07 |
| Linalyl acetate | 2.18 | 4.48 | 2.30 |
| Isobornyl acetate | 4.49 | 5.33 | 0.84 |
| Terpenyl acetate | 3.67 | 5.16 | 1.49 |
| Aldehyde MNA | 4.92 | 4.92 | 0.00 |
| delta Damascone | 3.78 | 4.24 | 0.46 |
| allyl (cyclohexyloxy)-acetate | 5.23 | 5.39 | 0.16 |
| Neobutenone ® Alpha | 6.01 | 6.05 | 0.04 |
| Methyl ionones | 4.56 | 4.61 | 0.05 |
| Cashmeran ® | 4.42 | 5.57 | 1.15 |
| Lilial ® | 5.96 | 5.98 | 0.02 |
| Methylnaphtylketone | 3.93 | 3.93 | 0.00 |
| Cedrenol | 5.12 | 5.14 | 0.02 |
| Hedione ® | 4.97 | 5.11 | 0.14 |
| ISO ® E Super | 4.26 | 4.27 | 0.01 |
| Crystal moss | 3.28 | 3.30 | 0.02 |
| Cetalox ® | 4.85 | 4.88 | 0.03 |
| Habanolide ® | 5.69 | 5.80 | 0.11 |

A panel of person (trained and not trained) described the overall olfactive effect provided by the invention composition as being more balanced, natural and a more round signature while the benchmark capsules provided an effect quite unbalanced or destructured where it was possible to detect specific raw materials rather than a harmonious fragrance. This is because some raw materials, which do not permeate sufficiently if they were to be encapsulated in a traditional method, are now present in the headspace at a quantity that rendered them perceivable.

As shown in the examples, the perfume oil of the microcapsules of the present invention can be designed with any number of different perfuming compounds with from one to around 50 different compounds being typical. Of course, higher amounts, even up to 100 different compounds, can be used based upon the preference of the perfumer and the desired overall odor character to be achieved. Generally, a few (i.e., 2 to 10) to an upper limit of around 25 different compounds are present in the microcapsules.

Example 2

Benchmark Microcapsules

Making Benchmark Microcapsules:

A perfume oil (40 g) (see composition below) was well-mixed with polyisocyanate monomers (Takenate® D 110N (2.19 g, 6 mmol NCO) and Desmodur® N100 (1.15 g, 6 mmol NCO)). Polyvinyl alcohol (PVOH Mowiol 18-88) (0.5445 g) was dissolved in de-ionized water (50.86 g) at 70° C. and once dissolved, the PVOH solution was cooled to room temperature. The oil mixture was then slowly added into the PVOH solution as the oil in water (O/W) emulsion was formed at room temperature using the homogenizer (Ultra Turrax, IKA T25 digital) set at 24000 rpm for 3 minutes. The O/W emulsion was then transferred into a 100 ml jacketed reactor and the stirrer (Eurostar power control-visc, IKA-WERKE) was set at 500 rpm. Guanazole (1.0 g, 10 mmol) was dissolved in the de-ionized water (5.38 g). The guanidine carbonate solution was added into the reactor delivered using a pump (Pump 11 Elite, Harvard Apparatus) set at a flow rate of 0.100 mL/min at room temperature, and this process took about 60 minutes. Once the addition was complete, the reaction temperature was increased from ambient temperature to 50° C. for the first 30 minutes, and then to 70° C. for the next 30 minutes. The reaction temperature was then maintained at 70° C. for another 2 hours. A Julabo heating immersion circulator (model MA, by Julabo Labortechnik GmbH, Seelbach, Germany) was used to maintain the reaction temperature. Afterwards, the reaction was cooled down to the ambient temperature.

Perfume Oil:

| Ingredient | Composition (wt %) |
|---|---|
| Rose Oxide | 20 |
| Dihydromyrcenyl acetate | 20 |
| Terpenyl acetate | 20 |
| Alpha neobutenone | 20 |
| Lilial ® | 20 |

Microcapsules According to the Invention

First Microcapsules:

Making of the First Microcapsules:

Same as the preparation of benchmark described above, except the only polyisocyanate monomer used was Desmodur® N100 (2.30 g, 12 mmol NCO) and Takenate® D 110N was not used.

Perfume Oil in First Microcapsules

| Ingredient | Composition (wt %) |
|---|---|
| Rose Oxide | 33.3 |
| Alpha neobutenone | 33.3 |
| Lilial ® | 33.3 |

Second Microcapsules

Making of the Second Microcapsules:

Same as the preparation of benchmark described above, except the only polyisocyanate monomer used was Desmodur® N100 (1.15 g, 6 mmol NCO) and Takenate® D 110N was not used.

Perfume Oil in the Second Microcapsules

| Ingredient | Composition (wt %) |
|---|---|
| Terpenyl Acetate | 50 |
| Dihydromyrcenyl Acetate | 50 |

The first and the second microcapsules were added at 3:2 weight ratio respectively, and this was used as the stock microcapsules slurry according to the invention.

2.1 Results in All Purpose Cleaner (APC) Application

APC base:

| Composition | Dosage (wt %) |
|---|---|
| Water | 88.8 |
| Nedol 91-8[1] | 5 |
| Marlon A 375[2] | 4 |
| Sodium Cumolsulfonate | 2 |
| Kathon CG | 0.2 |

[1] C9-11 Pareth-8
[2] Sodium Dodecylbenzenesulfonate

An amount of 10% diluted APC was prepared as follows: 0.1 g of benchmark or mixed capsules was mixed with 9.9 g of APC base (unthickened, CEN 07002, lot 1, LABO, APC standard base neutral) in a 200 mL glass bottle and it was filled up to 100 mL with cold tap water. An aliquot of 1 g of the above 10% diluted APC was applied to a ceramic tile of 10.8 cm×10.8 cm size. The tile was allowed to dry at room temperature for around 30 minutes in the hood and was subjected to analysis. This corresponds to fresh samples. In another case, the capsules in the undiluted APC base were allowed to age for a month and applied to the tiles using the method above. This corresponds to the aged samples.

Headspace After 16 Hours Equilibrium

Headspace collection of the tiles with APC was done as following: A dried tile with capsules was put into a 3 L reactor and all the outlets were closed to equilibrate overnight at room temperature. After the headspace reached equilibration, a Tenax tube was connected to a pump (calibrated speed at 130 mL min±5%) for absorbing the headspace. A charcoal tube was put on the other opening for filtered air to get in when the HS was pumped out of the reactor. Each reactor was pumped for 30 min (total volume 130 mL/min×30 min=3900 mL) for each sample.

TABLE 2

Analytical results from Headspace in all purpose cleaner application

| Sample | Sample type | Rose oxide (ng/L) | DHM acetate (ng/L) | α-terp. Acetate (ng/L) | Neobutenone (ng/L) | Lilial ® (ng/L) |
|---|---|---|---|---|---|---|
| benchmark | fresh | 3 | 2 | 2 | 2 | 3 |
| Invention | fresh | 6 | 4 | 3 | 5 | 6 |
| benchmark | aged | 8 | 9 | 5 | 3 | 16 |
| invention | aged | 23 | 26 | 16 | 13 | 22 |

The headspace intensity of all perfumery raw materials in the capsules according to the invention increase significantly. This shows that grouping the raw materials allows to tailor the intensity of the perfuming compound and improve the intensity of the perfuming ingredients especially those with high volatility and high odor threshold.

2.2 Results in a Deodorant Application

Deodorant Base:

| Composition | Dosage (wt %) |
|---|---|
| Brij 72 | 3.2 |
| Brij 721 | 0.7 |
| Arlamol E | 4.0 |
| DI water | 51.0 |
| Locron L | 40.0 |
| Perfume | q.s. |

An amount of 1% deodorant with capsules was prepared as follows: 0.1 g of either benchmark or mixed capsules was mixed well with 9.9 g of deodorant base in a 20 mL glass vial. An amount of 0.5 g deodorant with 1% capsules was applied to a piece of paper blotter of 5 cm×5 cm area. The blotter was rolled into the sample cell and its headspace was collected for 30 min at t=0 and t=6 hours.

The blotter was rolled and put into the tube of the GC cell. The tube was 1 cm above the bottom of the cell. The 39 wt % sodium bromide solution was employed to control the humidity of $N_2$ flow, resulting in a water activity of 0.738 at 22.4° C. $N_2$ flow rate was 40 mL/min and the water bath temperature was set at 32° C. After 0 and 6 hours, a pre-conditioned Tenax cartridge was inserted into the tube, where the cartridge was 4 cm above the cell. The HS was captured for 30 min. Then the HS samples were thermally desorbed (Perkin Elmer Turbo Matrix 650) and analyze by GC-MS (Agilent 6890/5975C).

GC-MS method: scan 80° C. for 2 min, 3° C./min to 180° C., then 10° C./min to 250° C. The MSD (EI, 70 eV) was operated in the selected ion monitoring mode for quantitative measurements. The GC was equipped with an Agilent DB-1 ms capillary column (30 m, 0.25 mm i.d. 0.25 μm film). The desorber parameters were: valve temperature 240° C., desorption temperature 240° C., transfer line 250° C., trap (−30° C. to 250° C. at 40° C./sec), purge time 1.0 min, desorption time 5 min, trap hold time 5 min, trap desorption flow time 0 min, cycle time 13 min, outlet split (5.2% injected), column flow 1.1 mL/min, desorption flow 50 ml/min For aged samples, the capsules in the deodorant base were allowed to age for a month, applied to the blotter and analysed in the same way as described above.

TABLE 3

Analytical results from Headspace in deodorant application

| Sample | Sample type | Sampling time | Rose oxide (ng/L) | DHM acetate (ng/L) | α-terp. Acetate (ng/L) | Neobutenone (ng/L) | Lilial ® (ng/L) |
|---|---|---|---|---|---|---|---|
| benchmark | fresh | t = 0 | 2247 | 1072 | 578 | 271 | 47 |
| mixture | fresh | t = 0 | 2439 | 3223 | 2098 | 520 | 145 |
| benchmark | fresh | t = 6 hours | 498 | 260 | 196 | 214 | 83 |
| mixture | fresh | t = 6 hours | 1078 | 1105 | 740 | 386 | 164 |
| benchmark | aged | t = 0 | 2047 | 1059 | 750 | 576 | 180 |
| mixture | aged | t = 0 | 2180 | 3005 | 2234 | 899 | 300 |
| benchmark | aged | t = 6 hours | 821 | 471 | 358 | 286 | 154 |

The headspace intensity of all perfumery raw materials in the capsules according to the invention increase significantly compared to benchmark. This shows that grouping the raw materials allows to tailor the intensity of the perfuming compound and improve the intensity of the perfuming ingredients especially those with high volatility and high odor threshold. Furthermore, the results still show improved intensity at the sixth hour, which signifies the long-lasting property of the invention. This result demonstrates that the invention can be applied to both body and home care applications.

Example 3

Benchmark Microcapsules

Making Benchmark Microcapsules

A perfume oil (40 g) (see composition below) was well-mixed with polyisocyanate monomers (Takenate® D 110N (2.19 g, 6 mmol NCO) and Desmodur® N100 (1.15 g, 6 mmol NCO)). Polyvinyl alcohol (PVOH Mowiol 18-88) (0.5445 g) was dissolved in de-ionized water (50.86 g) at 70° C. and once dissolved, PVOH solution was cooled to room temperature. The oil mixture was then slowly added into the PVOH solution as the oil in water (O/W) emulsion was formed at room temperature using the homogenizer (Ultra Turrax, IKA T25 digital) set at 24000 rpm for 3 minutes. The O/W emulsion was then transferred into a 100 ml jacketed reactor and the stirrer (Eurostar power control-visc, IKA-WERKE) was set at 500 rpm. Guanazole (1.0 g, 10 mmol) was dissolved in the de-ionized water (5.38 g). The guanidine carbonate solution was added into the reactor delivered using a pump (Pump 11 Elite, Harvard Apparatus) set at a flow rate of 0.100 mL/min at room temperature, and this process should take about 60 minutes. Once the addition was complete, the reaction temperature was increased from ambient temperature to 50° C. for the first 30 minutes, and then to 70° C. for the next 30 minutes. The reaction temperature was then maintained at 70° C. for another 2 hours. A Julabo heating immersion circulator (model MA, by Julabo Labortechnik GmbH, Seelbach, Germany) was used to maintain the reaction temperature. Afterwards, the reaction was cooled down to the ambient temperature.

Perfume oil:

| Name | Composition (wt %) |
| --- | --- |
| Romascone ® | 20 |
| Verdox | 20 |
| Dorisyl | 20 |
| Cyclosal | 20 |
| Salicynile | 20 |

Microcapsules According to the Invention

First Microcapsules

Making of First Microcapsules:

Same as the preparation of benchmark described above, except the only polyisocyanate monomer used was Desmodur® N100 (2.30 g, 12 mmol NCO) and Takenate® D 110N was not used.

Perfume Oil in First Microcapsules

| Name | Composition (wt %) |
| --- | --- |
| Cyclosal | 33.3 |
| Salicynile | 33.3 |
| Romascone ® | 33.3 |

Second Microcapsules

Making of Second Microcapsules:

Same as the preparation of benchmark described above, except the only polyisocyanate monomer used was Desmodur® N100 (2.30 g, 12 mmol NCO) and Takenate® D 110N was not used.

Perfume Oil in the Second Microcapsules

| Name | Composition (wt %) |
| --- | --- |
| Dorisyl | 50 |
| Verdox | 50 |

The first and the second microcapsules were added at 3:2 weight ratio respectively, and this is used as the stock microcapsules slurry according to the invention.

Results in Deodorant Application

An amount of 1% deodorant with capsules was prepared as follows: 0.1 g of either benchmark or mixed capsules was mixed well with 9.9 g of deodorant base (see example 2) in a 20 mL glass vial. An amount of 0.5 g deodorant with 1% capsules was applied to a piece of paper blotter of 5 cm×5 cm area. The blotter was rolled into the sample cell and its headspace was collected for 30 min at t=0 and t=6 hours.

The blotter was rolled and put into the tube of the GC cell. The tube was 1 cm above the bottom of the cell. The 39 wt % sodium bromide solution was employed to control the humidity of $N_2$ flow, resulting in a water activity of 0.738 at 22.4° C. $N_2$ flow rate was 40 mL/min and the water bath temperature was set at 32° C. After 0 and 6 hours, a pre-conditioned Tenax cartridge was inserted into the tube, where the cartridge was 4 cm above the cell. The HS was captured for 30 min. Then the HS samples were thermally desorbed (Perkin Elmer Turbo Matrix 650) and analyze by GC-MS (Agilent 6890/5975C).

GC-MS method: scan 80° C. for 2 min, 3° C./min to 180° C., then 10° C./min to 250° C. The MSD (EI, 70 eV) was operated in the selected ion monitoring mode for quantitative measurements. The GC was equipped with an Agilent DB-1 ms capillary column (30 m, 0.25 mm i.d. 0.25 µm film). The desorber parameters were: valve temperature 240° C., desorption temperature 240° C., transfer line 250° C., trap (−30° C. to 250° C. at 40° C./sec), purge time 1.0 min, desorption time 5 min, trap hold time 5 min, trap desorption flow time 0 min, cycle time 13 min, outlet split (5.2% injected), column flow 1.1 mL/min, desorption flow 50 ml/min

TABLE 4

Analytical results from Headspace in deodorant application

| Sample | Sample Type | Sampling time | Romascone (ng/L) | Verdox (ng/L) | Dorisyl (ng/L) | Cyclosal (ng/L) | Salicynile (ng/L) |
|---|---|---|---|---|---|---|---|
| Benchmark | Fresh | t = 0 | 886 | 418 | 457 | 101 | 121 |
| Mixture | Fresh | t = 0 | 5002 | 2778 | 2546 | 887 | 802 |
| Benchmark | Fresh | t = 6 hours | 376 | 331 | 287 | 110 | 122 |
| Mixture | Fresh | t = 6 hours | 968 | 721 | 986 | 358 | 464 |
| Benchmark | Aged | t = 0 | 1790 | 804 | 1033 | 262 | 267 |
| Mixture | Aged | t = 0 | 3158 | 1562 | 1618 | 1043 | 614 |
| Benchmark | Aged | t = 6 hours | 422 | 299 | 365 | 145 | 120 |
| Mixture | Aged | t = 6 hours | 909 | 1112 | 1261 | 609 | 543 |

The headspace intensity of all perfumery raw materials in the capsules according to the invention increase significantly compared to benchmark. This shows that grouping the raw materials allow us to tailor the intensity of the perfuming compound and improve the intensity of the perfuming ingredients especially those with high volatility and high odor threshold. Furthermore, the results still show improved intensity at the sixth hour, which signifies the long-lasting property of the invention. This example also demonstrates that the invention is applicable to different perfume oils.

Example 4

Benchmark Microcapsules

Making of Benchmark Microcapsules:

In a round bottom flask, oxalaldehyde (4.22 g, 40 wt % in water), 2,2-dimethoxyacetaldehyde (3.36 g, 60 wt % in water), 2-oxoacetic acid (1.44 g, 50 wt % in water), and 1,3,5-triazine-2,4,6-triamine (2.22 g) were dispersed in water (3.80 g). The pH was adjusted to 9.30 with sodium hydroxide (2.23 g, 30 wt % in water) and the reaction mixture was warmed up to 45° C. for 25 minutes to give a solution (pH=8.75). Finally, water (16.40 g) was added to the solution which was stirred for 5 minutes.

The solution of oligomers was introduced into a 200 mL reactor in the presence of 2,4-diamino-1,3,5-triazole (1.96 g) and a solution of Ambergum 1221 (66.38 g, 2 wt % in water, origin: Ashland). A solution of perfume oil (42.00 g) and Takenate® D-110N (5.28 g) was added and emulsified with Ultra-turrax at 21500 rpm for 2 min (pH=7.90). The pH was adjusted to 5.30 with formic acid (0.42 g, 30 wt % in water). Reaction mixture was heated at 45° C. for 1 h, at 60° C. for 1 h, at 80° C. for 3 h and finally cooled down to room temperature (pH=5.70).

Perfume Oil:

| Name | Composition (wt %) |
|---|---|
| Romascone ® | 20 |
| Verdox | 20 |
| Dorisyl | 20 |
| Cyclosal | 20 |
| Salicynile | 20 |

Microcapsules According to the Invention

First Microcapsules

Making of First Microcapsules:

Same as the preparation of benchmark described above, except 2.64 g of Takenate® D-110N was used.

Perfume Oil in First Microcapsules

| Name | Composition (wt %) |
|---|---|
| Cyclosal | 33.3 |
| Salicynile | 33.3 |
| Romascone | 33.3 |

Second Microcapsules

Making of Second Microcapsules:

Same as the preparation of benchmark described above, except 1.32 g of Takenate® D-110N was used.

Perfume Oil in the Second Microcapsules

| Name | Composition (wt %) |
|---|---|
| Dorisyl | 50 |
| Verdox | 50 |

The first and second microcapsules were added at 3:2 weight ratio respectively, and this is used as the stock microcapsules slurry according to the invention.

Results in Deodorant Application:

An amount of 1% deodorant with capsules was prepared as follows: 0.1 g of either benchmark or mixed capsules was mixed well with 9.9 g of deodorant base (see example 2) in a 20 mL glass vial. An amount of 0.5 g deodorant with 1% capsules was applied to a piece of paper blotter of 5 cm×5 cm area. The blotter was rolled into the sample cell and its headspace was collected for 30 min at t=0 and t=6 hours.

The blotter was rolled and put into the tube of the GC cell. The tube was 1 cm above the bottom of the cell. The 39 wt % sodium bromide solution was employed to control the humidity of $N_2$ flow, resulting in a water activity of 0.738 at 22.4° C. $N_2$ flow rate was 40 mL/min and the water bath temperature was set at 32° C. After 0 and 6 hours, a pre-conditioned Tenax cartridge was inserted into the tube, where the cartridge was 4 cm above the cell. The HS was captured for 30 min. Then the HS samples were thermally desorbed (Perkin Elmer Turbo Matrix 650) and analyze by GC-MS (Agilent 6890/5975C).

GC-MS method: scan 80° C. for 2 min, 3° C./min to 180° C., then 10° C./min to 250° C. The MSD (EI, 70 eV) was operated in the selected ion monitoring mode for quantitative measurements. The GC was equipped with an Agilent DB-1 ms capillary column (30 m, 0.25 mm i.d. 0.25 μm film). The desorber parameters were: valve temperature 240° C., desorption temperature 240° C., transfer line 250° C., trap (−30° C. to 250° C. at 40° C./sec), purge time 1.0 min, desorption time 5 min, trap hold time 5 min, trap desorption flow time 0 min, cycle time 13 min, outlet split (5.2% injected), column flow 1.1 mL/min, desorption flow 50 ml/min

TABLE 5

Analytical results from Headspace

| Sample | Sample Type | Sampling time | Romascone (ng/L) | Verdox (ng/L) | Dorisyl (ng/L) | Cyclosal (ng/L) | Salicynile (ng/L) |
|---|---|---|---|---|---|---|---|
| Benchmark | Fresh | t = 0 | 212 | 187 | 100 | 25 | 17 |
| Mixture | Fresh | t = 0 | 228 | 224 | 118 | 24 | 11 |
| Benchmark | Fresh | t = 6 hours | 18 | 20 | 18 | 10 | 8 |
| Mixture | Fresh | t = 6 hours | 63 | 993 | 352 | 32 | 17 |

The headspace intensity of all perfumery raw materials in the capsules according to the invention increase significantly compared to benchmark. This shows that grouping the raw materials allows to tailor the intensity of the perfuming compound and improve the intensity of the perfuming ingredients especially those with high volatility and high odor threshold. Furthermore, the results still show improved intensity at the sixth hour, which signifies the long-lasting property of the invention. This example also shows that the invention is applicable to different types of capsules.

What is claimed is:

1. A perfume composition comprising, a mixture of microcapsules including:
   (a) a first perfume microcapsule encapsulating a first perfume oil that has a LogT greater than −2.5 and a c log P greater than 2.5 and a volatility value of at least 30 μg/l air; and
   (b) a second perfume microcapsule encapsulating a second perfume oil that has a LogT less than −2.5 and a cLogP greater than 2.5 and a volatility value of at least 30 μg/l air.

2. The perfume composition of claim 1, wherein either of the first or second perfume oils, or both, comprises a mixture of perfuming compounds wherein at least 80% of the perfuming compounds each has the recited log T and cLogP and volatility values.

3. The perfume composition of claim 1, wherein either of the first or second perfume oils, or both, comprises a single perfuming compound or a mixture of perfuming compounds wherein each compound has the recited LogT and cLogP or volatility values.

4. The perfume composition of claim 3, wherein the perfuming compound or perfuming compounds in the first or second perfume oils, or both, each separately has a boiling point of 250° C. to 450° C.

5. A solution, comprising:
   a plurality of particles suspended in the solution;
   a propellant;
   an intermediary solvent soluble in the propellant; and
   a polymeric bonder adapted to bond the plurality of particles to a surface of an object to be imaged in three dimensions, the polymeric bonder being soluble in the intermediary solvent,
   wherein the solution is for the application of a contrast pattern to the surface of the object.

6. The perfume composition of claim 3, wherein the perfuming compound or perfuming compounds in the first or second perfume oils, or both, each separately has a volatility value of 30 to $5 \times 10^5$ μg/l air.

7. The perfume composition of claim 1, wherein the first or second perfume microcapsule(s) or both have a core/shell structure wherein the encapsulating material forms the shell while the perfume oil form the core, wherein one of the first or second microcapsules (a) has a wall made of a different resin than the other; (b) has a wall that includes a different amount of resin or monomer than the other; or (c) contains a different amount of perfume oil than the other; or wherein one of the first and second perfume microcapsules has a core/shell structure and the other has a matrix structure.

8. The perfume composition of claim 1, wherein the first microcapsule contains 50% by weight or less of the first perfume oil with each perfuming compound of the first perfume oil separately having a boiling point of 250° C. to 450° C., while the second microcapsule contains 50% by weight or more of the second perfume oil with each perfuming compound of the second perfume oil separately having a boiling point of 100° C. to 250° C.

9. A consumer product in the form of a home- or personal-care product that includes the perfume composition of claim 1.

10. The consumer product of claim 9, in the form of a detergent composition, a fabric softener, a hard surface cleaning composition, or a dishwashing composition.

11. The consumer product of claim 9 in the form of a shampoo, a hair conditioner, a shower or bath mousse, oil or gel, a deodorant, or an antiperspirant.

12. A method for increasing shelf life of a home- or personal care product containing a perfuming composition, which comprises providing the perfume composition as a mixture of microcapsules including:
   (a) a first perfume microcapsule encapsulating a first perfume oil ingredient that has a LogT greater than −2.5 and a cLogP greater than 2.5 and a volatility value of at least 30 μg/l air; and
   (b) a second perfume microcapsule encapsulating a second perfume oil ingredient that has a LogT less than −15 and a cLogP greater than 2.5 and a volatility value of at least 30 μg/l air.

13. The method of claim 12, wherein the consumer product is in the form of a detergent composition, a fabric softener, a hard surface cleaning composition, or a dishwashing composition.

14. The method of claim 12, wherein the consumer product is in the form of a shampoo, a hair conditioner, a shower or bath mousse, oil or gel, a deodorant, or an antiperspirant.

* * * * *

UNITED STATES PATENT AND TRADEMARK OFFICE
CERTIFICATE OF CORRECTION

PATENT NO. : 9,487,733 B2  
APPLICATION NO. : 14/423064  
DATED : November 8, 2016  
INVENTOR(S) : Budijono et al.

Page 1 of 1

It is certified that error appears in the above-identified patent and that said Letters Patent is hereby corrected as shown below:

In the Claims

Column 27:
Lines 39-40 (Claim 1, Lines 4-5), delete "c log P" and insert -- cLogP --.
Line 49 (Claim 2, Line 4), delete "log T" and insert -- LogT --.
Delete Lines 60-67 (Claim 5, Lines 1-8), and insert:
-- 5. The perfume composition of claim 3, wherein the perfuming compound or perfuming compounds in the first or second perfume oils, or both, each separately has a boiling point of 100° C. to 250° C. --.

Column 28:
Delete Lines 1-2 (Claim 5, Lines 9-10).
Line 57 (Claim 12, Line 11), delete "-15" and insert -- -2.5 --.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*